(12) United States Patent
Yamamoto et al.

(10) Patent No.: US 7,175,636 B2
(45) Date of Patent: Feb. 13, 2007

(54) ENDOSCOPIC SUTURING INSTRUMENT

(76) Inventors: Tetsuya Yamamoto, c/o Olympus Optical Co., Ltd. 2-3 Kuboyama-cho, Hachioji-shi (JP) 192-8512; Sydney Sheung Chee Chung, House 6, 26th Street, Hong Lok Yuen, Tai Po, New Territories, Hong Kong (CN)

( * ) Notice: Subject to any disclaimer, the term of this patent is extended or adjusted under 35 U.S.C. 154(b) by 571 days.

(21) Appl. No.: 10/231,086

(22) Filed: Aug. 30, 2002

(65) Prior Publication Data

US 2003/0045891 A1 Mar. 6, 2003

Related U.S. Application Data

(60) Provisional application No. 60/315,925, filed on Aug. 31, 2001.

(51) Int. Cl.
*A61B 17/04* (2006.01)
(52) U.S. Cl. ....................... 606/144; 606/139
(58) Field of Classification Search ................ 606/139, 606/144–148; 289/17
See application file for complete search history.

(56) References Cited

U.S. PATENT DOCUMENTS

| | | | | | |
|---|---|---|---|---|---|
| 2,327,353 | A | * | 8/1943 | Karle | ........................ 606/146 |
| 4,484,580 | A | | 11/1984 | Nomoto et al. | |
| 4,841,888 | A | * | 6/1989 | Mills et al. | ................. 606/145 |
| 6,086,601 | A | | 7/2000 | Yoon | |

* cited by examiner

*Primary Examiner*—Julian W. Woo
(74) *Attorney, Agent, or Firm*—Frishauf, Holtz, Goodman & Chick, P.C.

(57) ABSTRACT

An endoscopic suturing instrument is equipped with a needle mounted at the distal end of the suturing instrument for the purpose of living-tissue punctures. An engaging mechanism is provided at least at the distal end of the needle for the purpose of connecting the thread while allowing it to move freely, and the suturing instrument includes a needle-driving mechanism to drive the needle. A loop-creating mechanism is used to create a first loop in the thread, by loosening the thread connected to the engaging mechanism. A catching mechanism is provided at the distal end of the suturing instrument to be inserted through the first loop to catch the thread. The thread caught by the catching mechanism can be moved freely. The needle-driving mechanism and the catching mechanism are mechanically coupled.

22 Claims, 24 Drawing Sheets

ENDOSCOPIC SUTURING INSTRUMENT

CROSS-REFERENCE TO RELATED APPLICATIONS

This application claims the benefit of U.S. Provisional Application to Sydney Sheung Chee Chung et al, entitled "Endoscopic Suturing Device," application No. 60/315,925, filed Aug. 31, 2001.

BACKGROUND OF THE INVENTION

This invention relates to a suturing instrument with which to arrest hemorrhaging or to suture or anastomose the tissue in the lumen using a flexible endoscope.

In recent years, there has been remarkable progress in the development of suturing instruments with which to suture the tissue in the lumen or hemostasis site. In particular, the development of suturing instruments applicable to open surgery and bellybutton surgery, in which the operation is performed through several fistulas created in the abdomen, has been attempted through several experiments.

For example, U.S. Pat. No. 6,086,601 (InBae Yoon) is a surgical suturing instrument intended for application to open surgery or bellybutton surgery. It consists of a needle driver that rotates freely in a rigid barrel and a needle catcher, which are operated with handles mounted on the main body at its proximal end. A needle with thread is delivered and held alternately between them to suture the tissue.

As another example, U.S. Pat. No. 4,484,580 (Janome Sewing Machine Co.) is a surgical suturing instrument intended for application to open surgery or belly button surgery. It consists of a curved needle, which has a needle eye and an oblong groove, and which is fixed to a needle bar and a shuttle thread connected through the needle eye and oblong groove to a shuttle which is fixed between a shuttle claw and a shuttle holder of a shuttle holder member. The suturing procedure is as follows: The tissue is punctured by the curved needle through the needle bar. The shuttle thread coming out of the tissue forms a loop of a crescent. Then the shuttle is wound around the loop of crescent by the shuttle holder member to form a stitch.

However, as U.S. Pat. No. 6,086,601 (InBae Yoon) was originally intended for use in open surgery or bellybutton surgery, it cannot be used in conjunction with an endoscope, which bends flexibly so as to be inserted into digestive organs. Even if the needle driver or other driving shaft is replaced by a flexible wire so as to make it applicable to a flexible endoscope, the force with which the needle driver grasps the needle is so weak that the needle may easily fall off from the needle driver when puncturing, causing the puncture to fail. In addition, every time the needle is delivered from the needle driver to the needle catcher for a stitch, it must be returned from the needle catcher to the needle driver. This requires a complicated operation. Moreover, to deliver the needle between the needle driver and the needle catcher in a limited range, they must be rotated many times to adjust for the difference in their loci. This takes a lot of time.

Similarly, as in U.S. Pat. No. 6,086,601 (InBae Yoon), U.S. Pat. No. 4,484,580 (Janome Sewing Machine Co.) was developed for use in open surgery or bellybutton surgery and cannot be used in conjunction with an endoscope, which bends flexibly so as to be inserted into digestive organs. In addition, as in U.S. Pat. No. 6,086,601 (InBae Yoon), even if the needle bar or the rod portion of U.S. Pat. No. 4,484,580 (Janome Sewing Machine Co.) is replaced with a flexible coil, it will not work because a shuttle thread long enough to perform continuous stitches must be laid along the shuttle and the curved needle, causing the shuttle thread to be seen in the view field or disturbing the curved needle at the time of puncture. Moreover, it can be very poor in suture efficiency or even make suture work itself impossible because it is very difficult to thrust the curved needle through the tissue in actual practice, as shown with respect to curved needle 300 and tissue 301 in FIG. 43. The practice, as shown in FIG. 5 in the specification of U.S. Pat. No. 4,484,580 (Janome Sewing Machine Co.), cannot be realized without the tissue in the vicinity of the part being held tight.

SUMMARY OF THE INVENTION

To solve the problems above in implementing a suturing instrument that provides continuous stitches in operation under flexible endoscopy, the endoscopic suturing instrument is equipped with a needle mounted at the distal end of the suturing instrument for the purpose of living-tissue punctures. An engaging means is provided at least at the distal end of the needle for the purpose of connecting the thread while allowing it to move freely, and it is equipped with a needle-driving means to drive the needle. A loop-creating means, used to create a first loop in the thread, is provided for the suturing instrument. The first loop is formed by loosening the thread connected to the engaging means. A catching means to be inserted through the first loop to catch the thread is provided at the distal end of the suturing instrument. The thread caught by the catching means can be moved freely. The needle-driving means and the catching means are integrated into one.

The suturing instrument, integrated into or detachably mounted onto the distal end of an endoscope, is equipped with a needle that is integrated into or detachably mounded onto a driving member. The needle has a needle eye through which the thread may be inserted. The thread is inserted through the needle eye while it is inserted in a channel of the endoscope from the proximal end to the distal end or laid along the external surface of the endoscope.

The endoscope with the suturing instrument mounted on its tip is introduced in the suture site in the lumen with the needle placed inside the protection member.

The operating portion for controlling the needle provided at the proximal end of the endoscope is used to place the needle at the specified position. Then, the angulation of the endoscope is adjusted so that the suturing instrument will come in contact with the suture site. In this state, the operating portion for controlling the needle is operated to start the puncture.

When the tissue is punctured, the cam mechanism allows the thread to be grasped by the catching means. With the thread grasped, the needle is restored to the position specified. Then, the suturing instrument is moved to the second suture site, a little distant from the first, to perform the second puncture. By this time, the thread grasped by the catching means has formed a loop as a result of the movement, and the catching means is held in a position so that the needle may pass through the loop. As soon as at least part of the needle passes through the loop, the catching means is removed from the thread having the loop. Then, the cam mechanism allows the thread to be grasped by the catching means again. Through the repetition of the procedure above, continuous stitches are formed. When the last stitch is completed, the endoscope is removed from the body with the loop in the thread grasped by the catching means, and both ends of the thread are fixed to the means to prevent the thread from loosening. The suturing procedure is thus completed.

DETAILED DESCRIPTION

A first example of an embodiment of the present invention [Example 1] is shown in FIG. 1 through FIG. 21.

Figure 1:
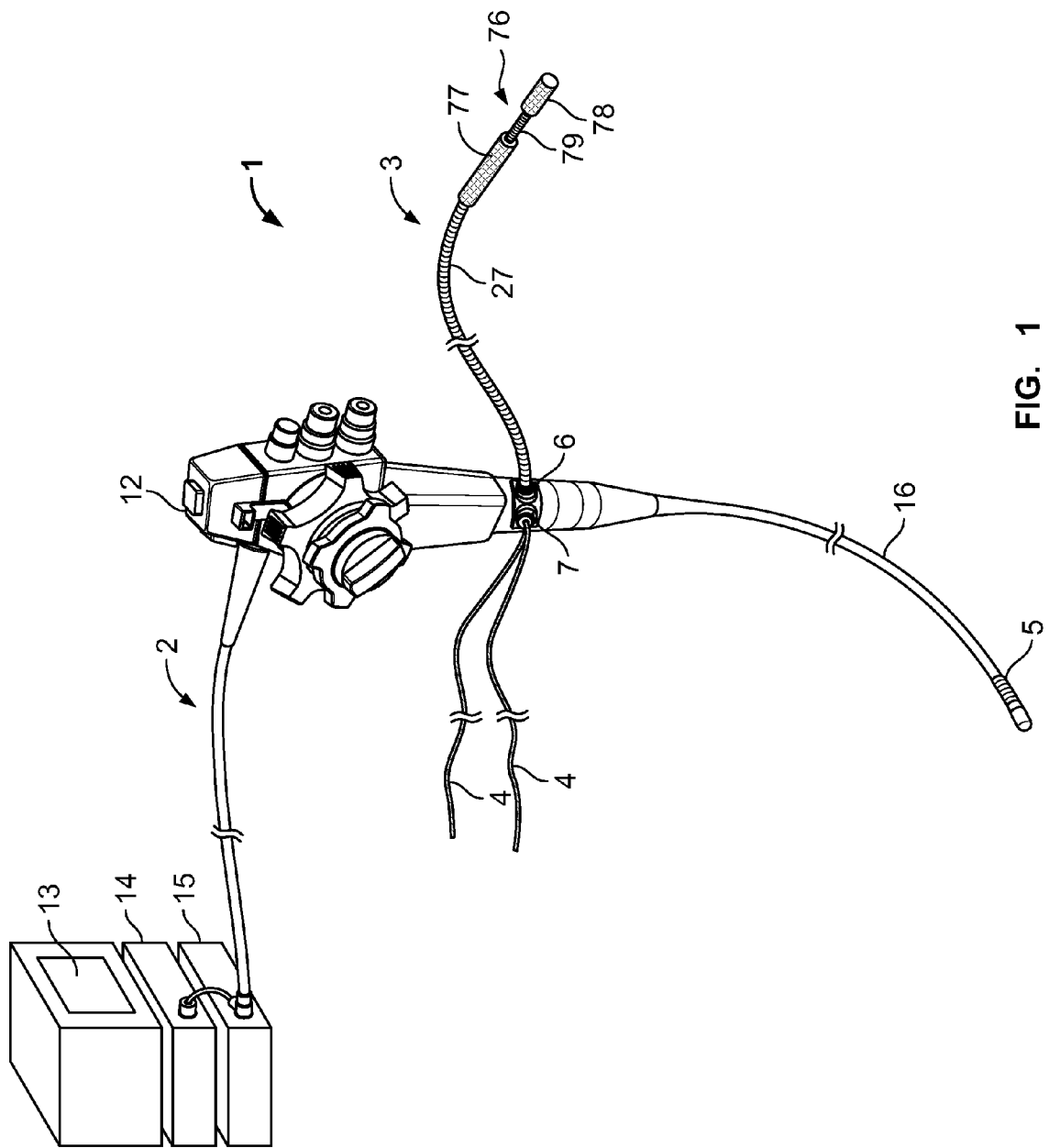
FIG. 1 shows an endoscopic suturing instrument according to a first embodiment.
Figure 2:
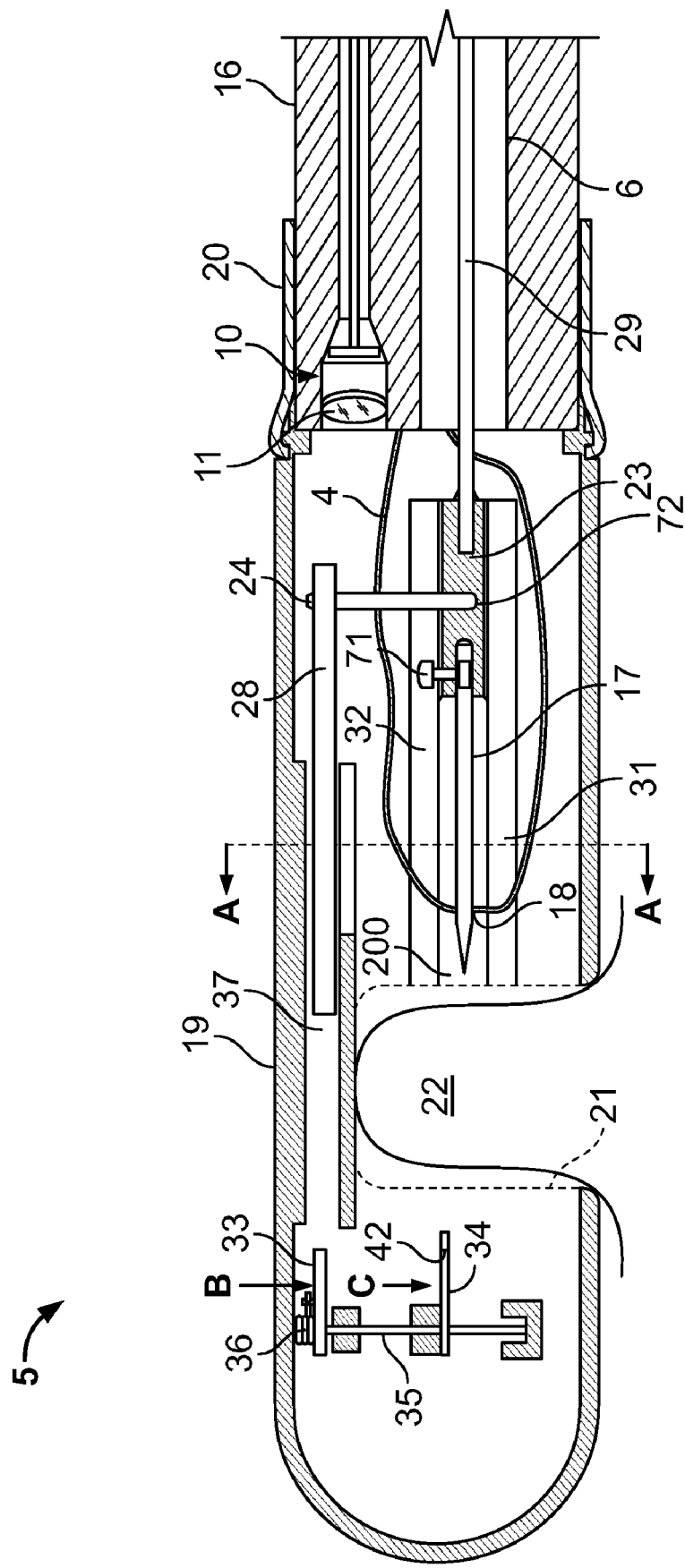
FIG. 2 is an enlarged sectional view of the distal end of the endoscope 12.
Figure 3:
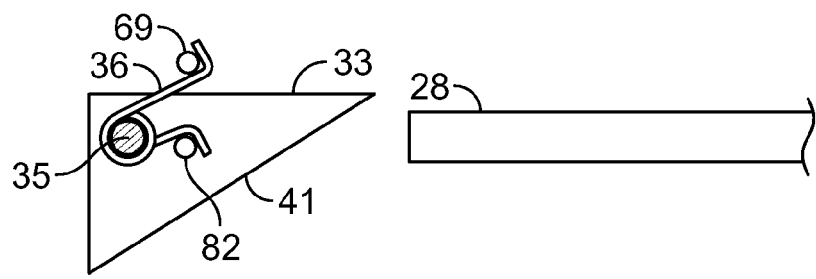
FIG. 3 is a view along direction B in FIG. 2.
Figure 4:
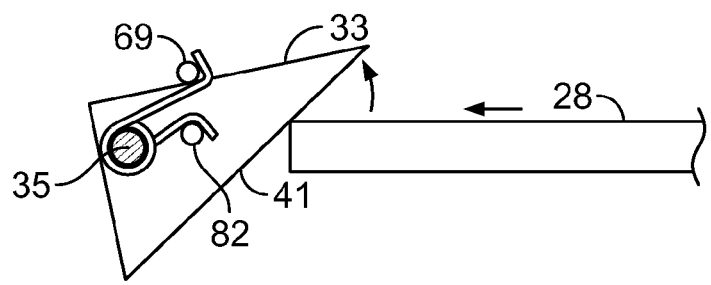
FIG. 4 is a view along direction B in FIG. 2 when rod 28 rotates cam 33.
Figure 5:
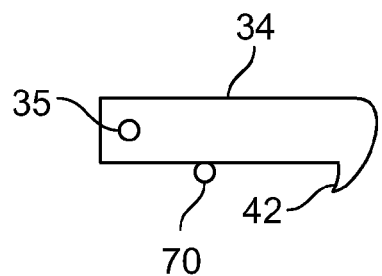
FIG. 5 is a view along direction C in FIG. 2.
Figure 6:
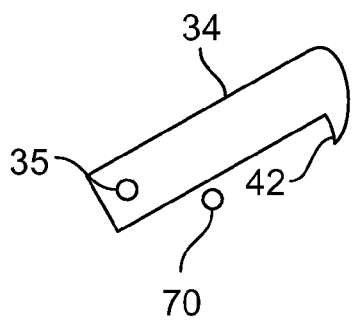
FIG. 6 is a view along direction C in FIG. 2 when rod 28 rotates cam 33.
Figure 7:
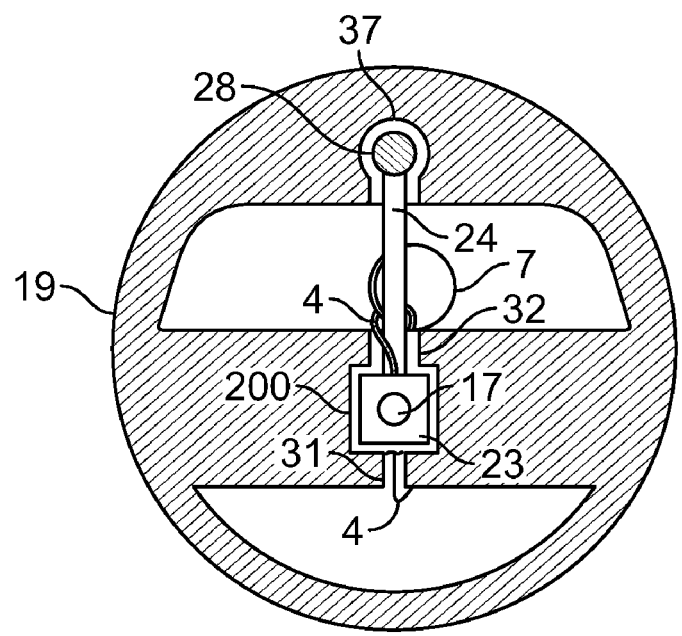
FIG. 7 is a cross-sectional view along lines A-A in FIG. 2.
Figure 44:
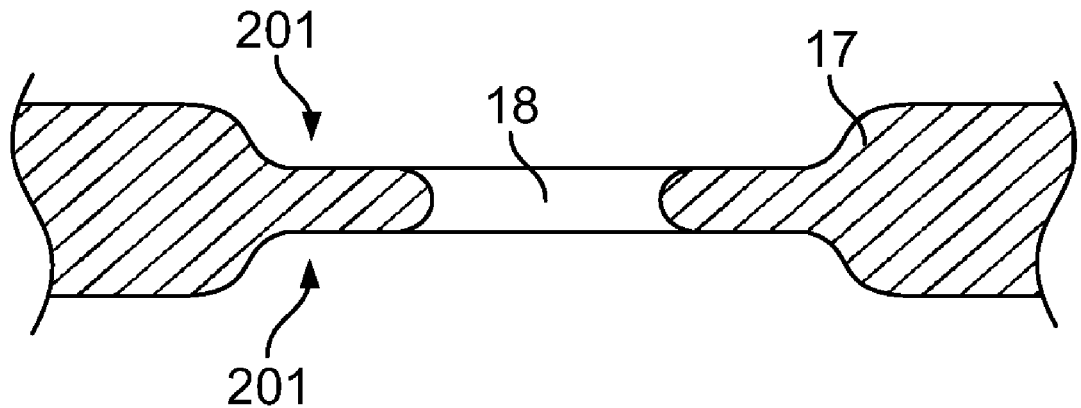
FIG. 44 shows a depression around the eye of the needle in the suturing instrument according to the first embodiment.

As shown in FIG. 1, the endoscopic suturing instrument system 1 consists of an endoscope system 2, a suturing instrument 3, thread 4, and a tissue-protection member 5. The endoscope system 2 is an ordinary videoscope system consisting of an endoscope 12, an image-processing equipment 14, a light source 15, and an observation monitor 13. An endoscope 12, equipped with two instrument channel ports 6, 7, is used, but an endoscope with one channel or one with a tube attached to the flexible portion 16 using medical tape to provide a channel may be used. As shown in FIG. 2 and FIG. 7, the endoscope 12 is equipped at its tip with a CCD camera 10, light guides (not shown), instrument channel ports 6, 7, and a nozzle (not shown) for cleaning the COD camera lens 11. In this example, a video scope is used. However, a fiberscope may also be used. The suturing instrument 3 is inserted in the instrument channel port 6. The thread 4 inserted through the needle eye 18 provided in the straight needle 17 of the suturing instrument 3 extends through the instrument channel port 7 to its proximal end. This provides an engaging means to allow connecting the thread to the needle while allowing it to move freely. In this example, a depressed portion 201 is formed around the needle eye 18 as shown in FIG. 44, in order to reduce puncture resistance. Also, in this example, the suturing instrument 3 is provided in the instrument channel 6 of the video scope 12. However, it may also be built into the endoscope 12. As shown in FIG. 2, the tissue-protection member 5 consists of protection portion 19, at least part of which is transparent, and the fixing portion 20 made of an elastomer resin such as silicon rubber. The protection portion 19 is joined with the fixing portion 20 by injection or adhesion. The tissue protection member 5 thus constituted is detachably fixed to the flexible portion 16. This is implemented by pressing the fixing portion 20 into the distal end of the flexible portion 16. The protection portion 19 is provided with a slit 21, through which the tissue 22 is sucked into the protection portion 19 when the sucking function through the instrument channel port 6 or 7 of the endoscope is used to suck in the tissue 22. In addition, as shown in FIG. 2 and FIG. 7, the protection portion 19 is provided with a groove 200 with which to guide the needle-fixing portion 23 that fixes the straight needle 17. The groove 200 is provided with slits 31 and 32 so that the thread 4 inserted through the needle eye 18, the guide pin 24, and the screw 71 may pass through. At the distal end of the needle-fixing portion 23, the straight needle 17 is detachably connected by the screw 71. At the proximal end of the needle-fixing portion 23, the operating wire 29 (forming a needle driving means) is brazed or soldered to it. A hole 72 is punched in the center of the needle-fixing portion 23 so as to fit the end of the guide pin 24. The other end of the guide pin 24 is fixed to the proximal end of the rod 28. The rod 28 can slide along the inside of the hole 37 created in the protection portion 19. On the locus of the rod 28, as shown in FIG. 2 through FIG. 4, a cam 33 is fixed at one end of the shaft 35 while being allowed to rotate freely. It rotates counterclockwise when the rod 28 is pushed against the oblique portion 41 of the cam 33, and the shaft 35 rotates in the same way at the same time, as shown in FIG. 3 and FIG. 4. A thread catch member 34 having a hook 42 (and forming a catching means) with which to catch the thread 4 is fixed to the shaft 35. As shown in FIG. 3 and FIG. 4, a force is applied to the shaft 35 by the spring 36, which is supported at positions 82 and 69, so that it may constantly rotate clockwise. The rotation is restricted by the stopper 70, as shown in FIG. 5, although the way the stopper 70 is fixed to the protection portion 19 is not shown in the diagram. Thus, when the cam 33 is rotated counterclockwise by the rod 28, the thread catch member 34 will also rotate counterclockwise, as shown in FIG. 5 and FIG. 6.

Figure 8:
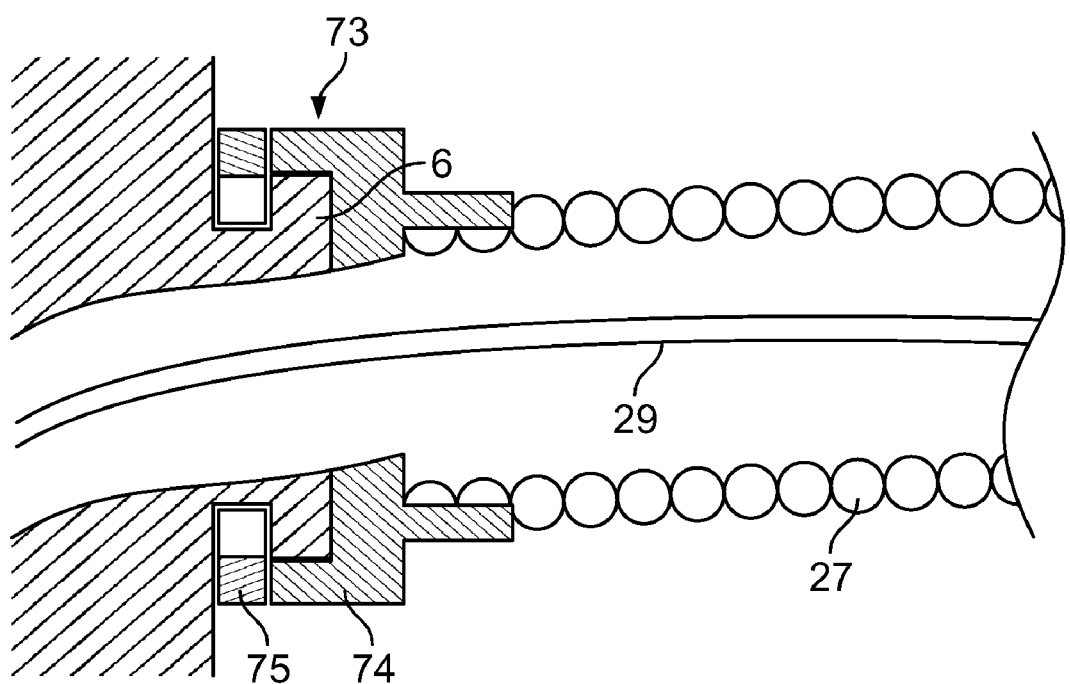
FIG. 8 shows the connection point of the suturing instrument 3 to the instrument channel port 6.

As shown in FIG. 8, the proximal end of the suturing instrument 3 is detachably connected to the instrument channel port 6 by the coil-holding member 73, which is fixed at the distal end of the coil 27. The coil-holding member 73 consists of a holding portion 74 and a lock portion 75. The lock portion 75 is constructed so that it will slide on the holding portion 74 vertically to the sheet surface. By sliding the lock portion 75, the coil-holding member 73 is detachably fixed to the instrument channel port 6.

As shown in FIG. 1, the operating portion 76 is fixed to the proximal end of the coil 27. The operating portion 76 consists of a grip A (77), grip B (78), and pipe 79. The operating wire 29, as shown in FIG. 2, is inserted into the pipe 79 through the coil 27, and it is fixed together with the grip B 78 at the proximal end of the pipe 79. The grip A 77 is fixed at the proximal end of the coil 27. In this makeup, as the grip B 78 slides backward or forward, the operating wire 29 will go backward or forward through the pipe 79 so as to drive the straight needle 17 mounted at its distal end and the thread catch member 34 through the rod 28.

Figure 9B:
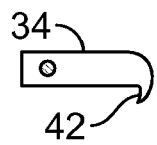
FIG. 9B is a cross-sectional view along lines D—D in FIG. 9A.
Figure 9A:
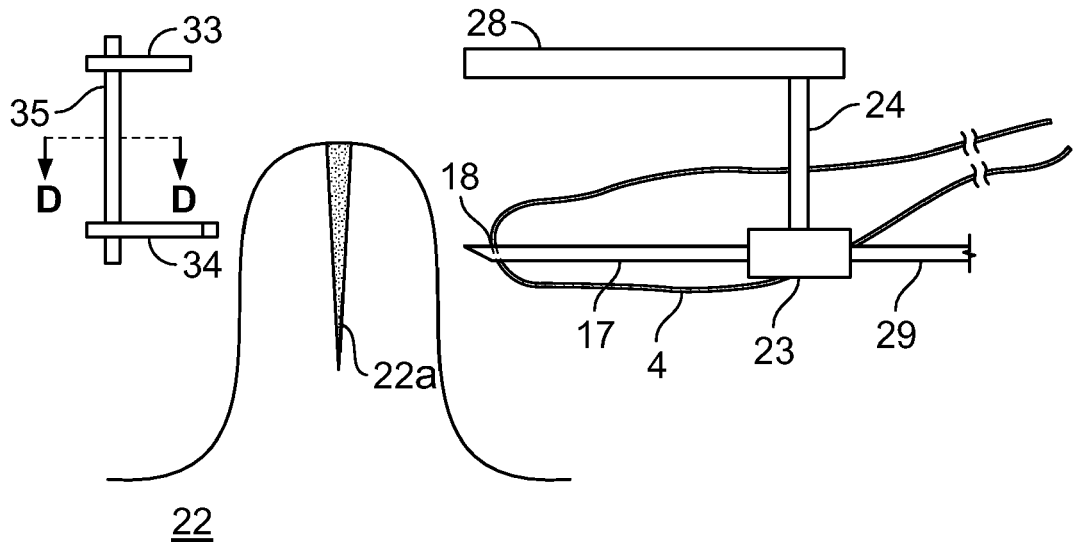
FIGS. 9A, 10A, 11A, 12A, 13A, 14A, 15A, 16A, 17A and 18A are views of steps in a suturing procedure according to the first embodiment.

A suturing procedure using Example 1 is shown in FIGS. 9 through 21. As shown in FIGS. 9A and 9B, the thread 4 is inserted through the needle eye 18 of the straight needle 17, and the suction function of the endoscope is used to suck in the tissue 22, the suture site (including wound 22a) included.

Figure 10B:
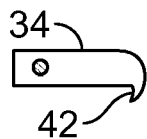
FIG. 10B is a cross-sectional view along lines E—E in FIG. 10A.
Figure 10A:
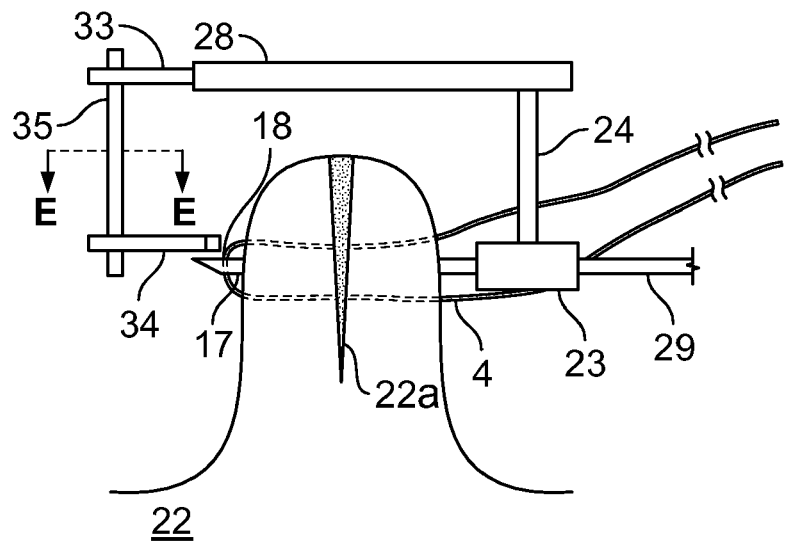

As shown in FIGS. 10A and 10B, the grip B 78 is pushed forward to thrust the straight needle 17 through the tissue 22.

Figure 11B:
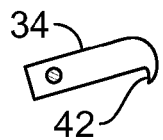
FIG. 11B is a cross-sectional view along lines F—F in FIG. 11A.
Figure 11A:
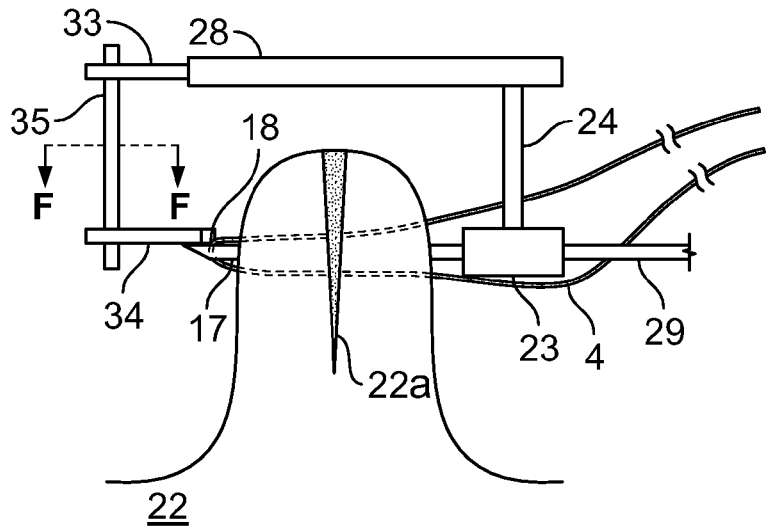

As shown in FIGS. 11A and 11B, as the straight needle 17 is further pushed forward, the rod 28 comes in contact with the cam 33, causing the shaft 35 to rotate counterclockwise, while the thread catch member 34 is rotated until it comes to the position shown in FIGS. 11A and 11B.

Figure 12B:
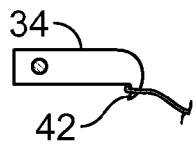
FIG. 12B is a cross-sectional view along lines G—G in FIG. 12A.
Figure 12A:
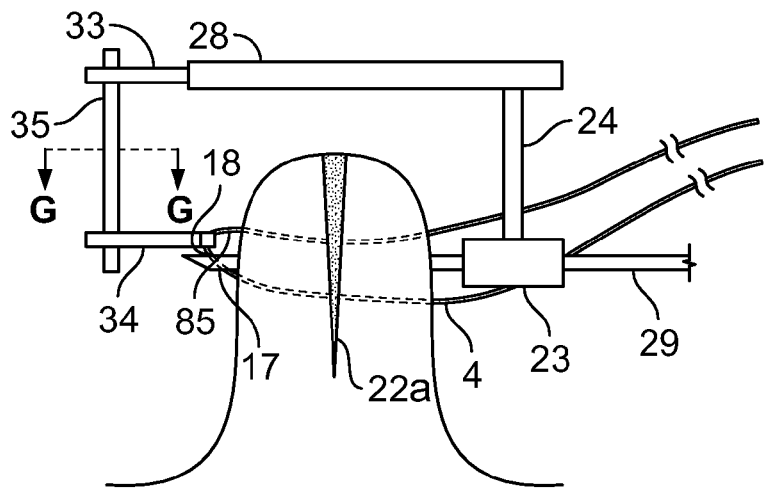

Then, as shown in FIGS. 12A and 12B, as the grip B 78 is gradually withdrawn, a loop portion 85 is formed between the straight needle 17 and the thread 4. When the contact between the rod 28 and the cam 33 is released, the thread catch member 34 rotates clockwise to return to the position shown in FIGS. 12A and 12B, where the thread is caught by the hook 42.

Figure 13B:
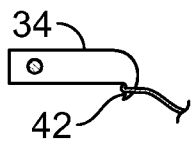
FIG. 13B is a cross-sectional view along lines H—H in FIG. 13A.
Figure 13A:
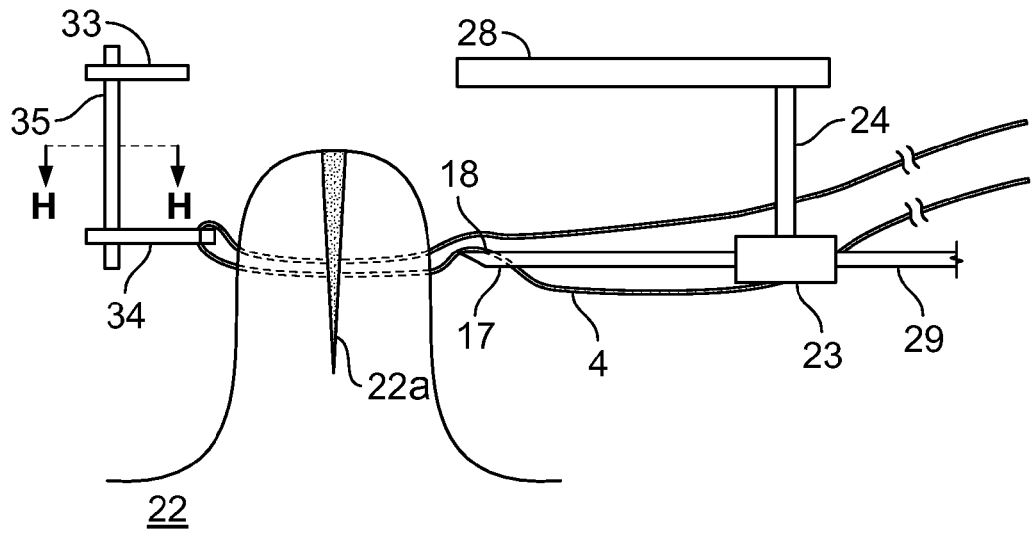

As shown in FIGS. 13A and 13B, the grip B 78 is further withdrawn to remove the straight needle 17 from the tissue 22, and the distal end of the flexible portion 16 is moved backward with respect to the sheet surface.

Figure 14B:
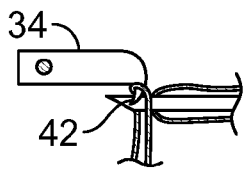
FIG. 14B is a cross-sectional view along lines I—I in FIG. 14A.
Figure 14A:
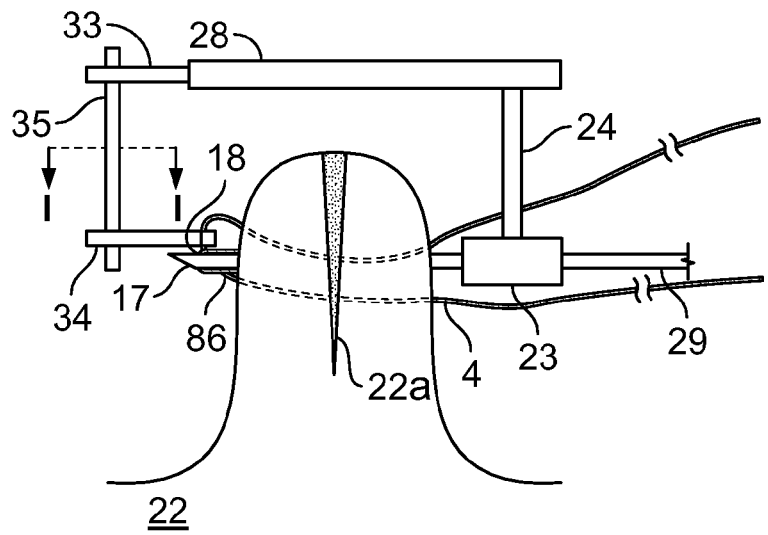

Then, in the same way as explained above, the suction function of the endoscope is used to suck in the tissue 22, and the tissue 22 is punctured by the straight needle 17, as shown in FIGS. 14A and 14B, when the movement of the flexible portion 16 causes the thread 4 caught by the hook 42 to form a loop portion 86. The straight needle 17 passes through the loop portion 86 after the tissue is punctured.

Figure 15B:
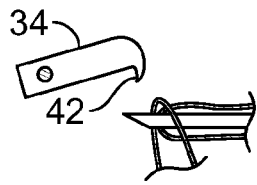
FIG. 15B is a cross-sectional view along lines J—J in FIG. 15A.
Figure 15A:
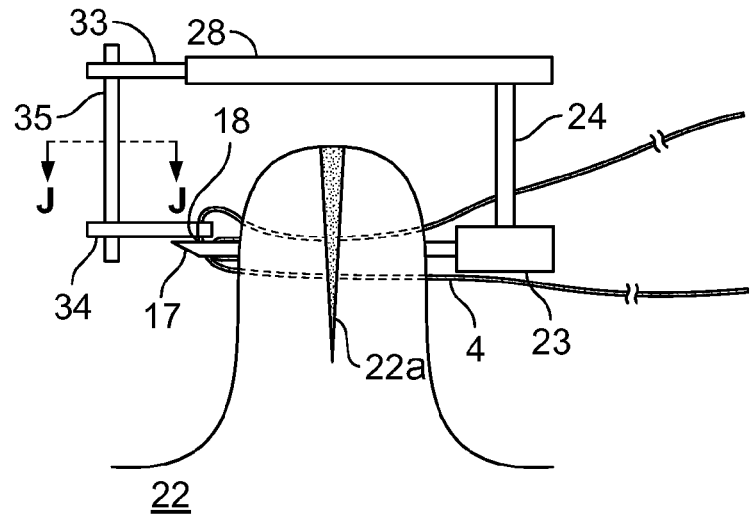

As shown in FIGS. 15A and 15B, when the straight needle 17 is pushed forward as explained above, the rod 28 comes in contact with the cam 33, causing the thread catch member 34 to rotate counterclockwise. Thus, the thread 4 is released from the hook 42.

Figure 16B:
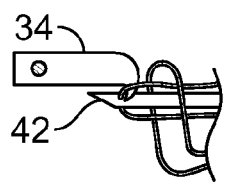
FIG. 16B is a cross-sectional view along lines K—K in FIG. 16A.
Figure 16A:
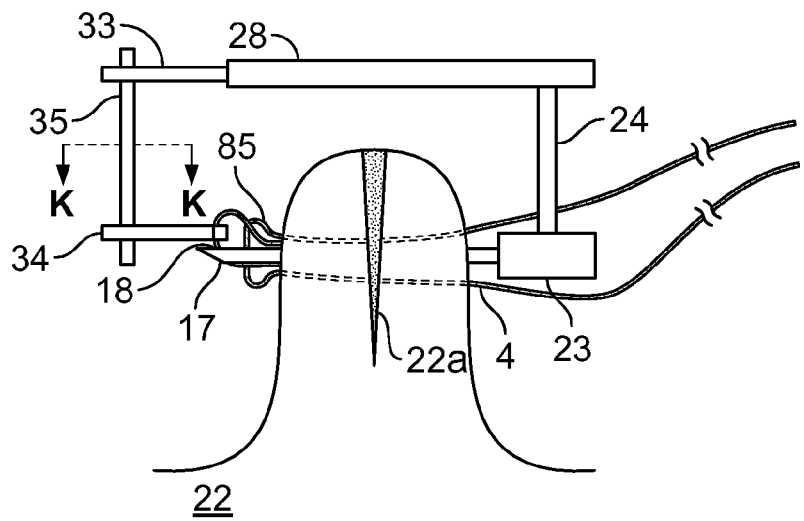

Then, as shown in FIGS. 16A and 16B, as the straight needle 17 is withdrawn to restore to the original position, the same loop portion 85 as shown in FIGS. 12A and 12B is formed, and the thread 4 is caught by the hook 42.

Figure 17B:
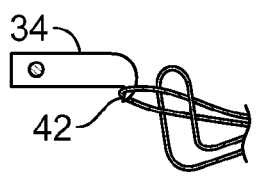
FIG. 17B is a cross-sectional view along lines L—L in FIG. 17A.
Figure 17A:
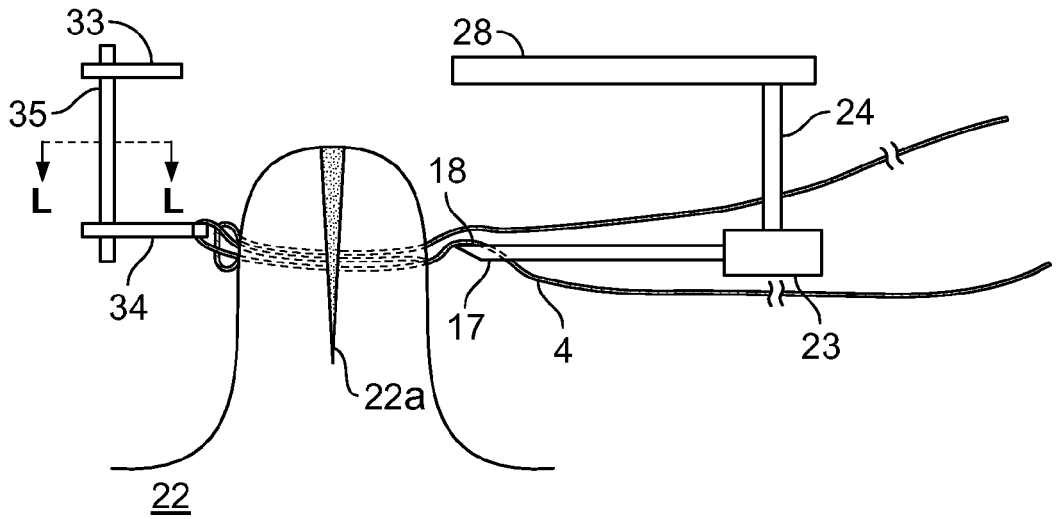
Figure 18B:
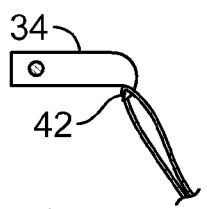
FIG. 18B is a cross-sectional view along lines M—M in FIG. 18A.
Figure 18A:
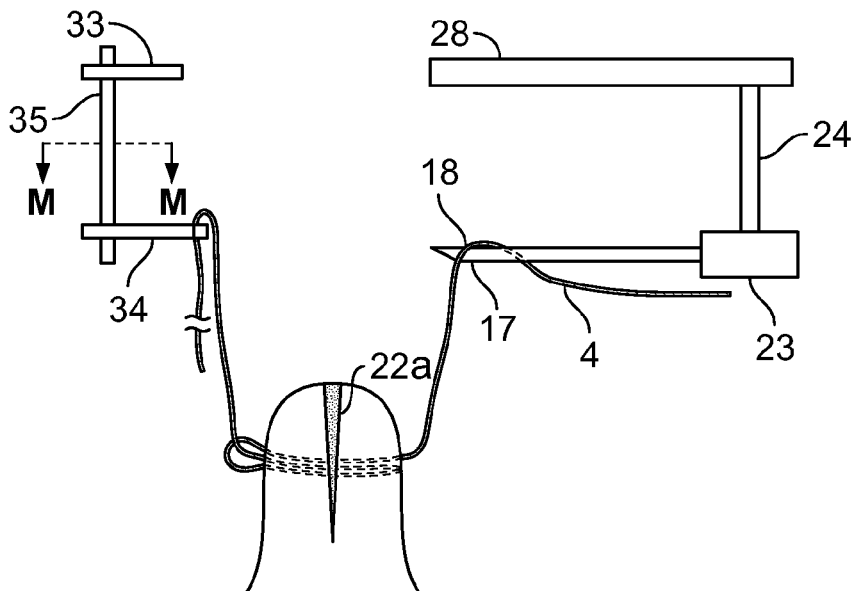

Then, as shown in FIGS. 17A and 17B and FIG. 1, the grip B 78 is further withdrawn to remove the straight needle 17 from the tissue 22.

Figure 19:
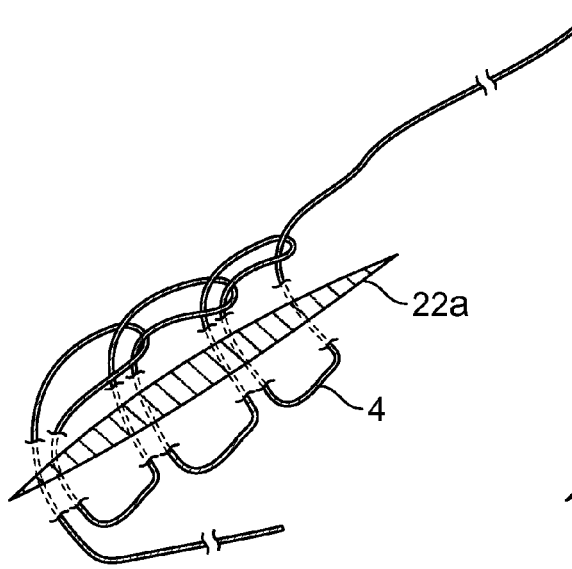
FIG. 19 shows continuous stitches in a wound.
Figure 20:
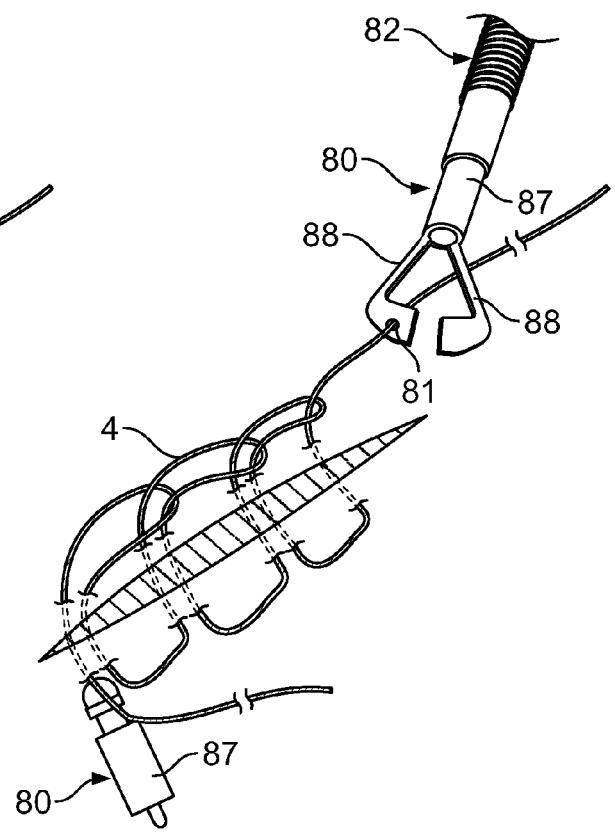
FIG. 20 shows a ligating procedure.
Figure 21:
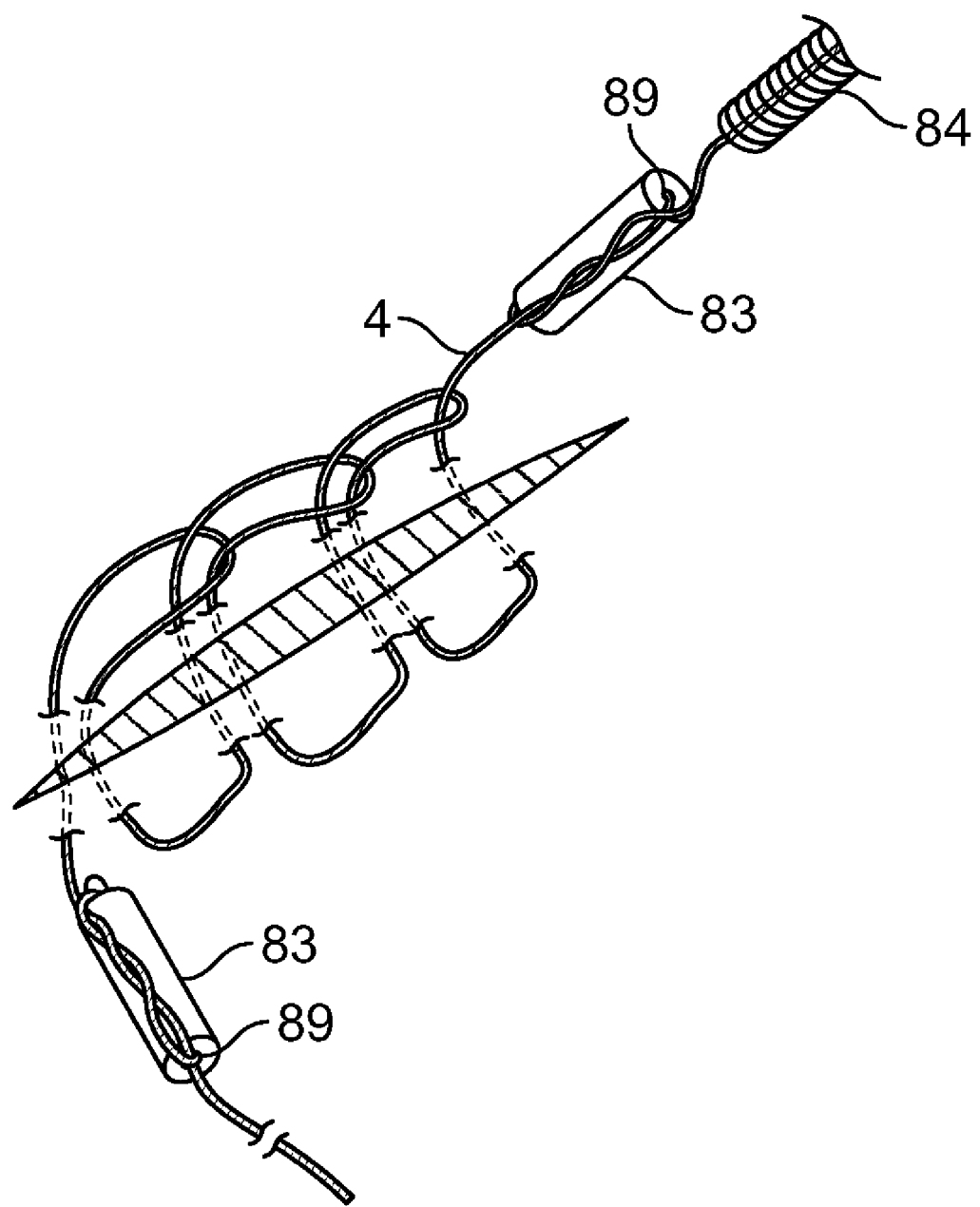
FIG. 21 shows an alternative ligating procedure.

After this, the procedure, as shown in FIGS. 14 through 17 is repeated to create continuous stitches shown in FIG. 19. In the last stitch, as shown in FIGS. 17A, 17B, 18A and 18B, the flexible portion 16 is removed from the living body with the straight needle 17 withdrawn from the tissue 22, and the thread pulled out from the lumen is ligated with the ligating members 80 and 83, as shown in FIG. 20 and FIG. 21. The ligation may extra corporeally be performed by simply creating a knot, which is then pushed into the body with a knot pusher. In addition, the ligating member 80 is a ligation instrument equipped with a pair of arms 88 made of elastic material. The distal end of one of the arms is provided with a hole 81 through which the thread 4 may be inserted. With the thread acting as a guide, the ligating member 80 is advanced to the ligation side, where the arms 88 are closed to affix the thread 4 to the ligating member 80 by withdrawing into the pipe 87 through the operation of the operating portion, which is not shown in the diagram. The ligating member 83 is made up of elastic material having a small hole 89. The ligating member 83 is ligated in the following way: as shown in FIG. 21, the thread 4 is inserted through the hole 89 at least once, and then one or more knots are created. Then, the sleeve portion of the ligating member 83 is pushed in with the pusher 84 to fix the end of the thread.

An embodiment according to Example 1 has a number of advantages. First, tissue is sequentially stitched through a flexible endoscope.

Held securely in the needle-fixing portion, the needle will not come off as it often does from the needle holder. Thus, the needle accurately punctures tissue without fail. Since the need for alternately re-holding of the needle is eliminated, operation is simpler.

The tissue is held tightly during the suturing procedure when the suction function of the endoscope is used so that the procedure is easier.

There is no limitation to the length of thread to be loaded, so long wounds may be sutured in continuous stitches while the endoscopic view is seldom disturbed.

The needle is detachable from the needle-fixing portion so that disposable needles may be used.

A second example of an embodiment of the present invention [Example 2] is shown in FIG. 22 through FIG. 42.

Figure 22:
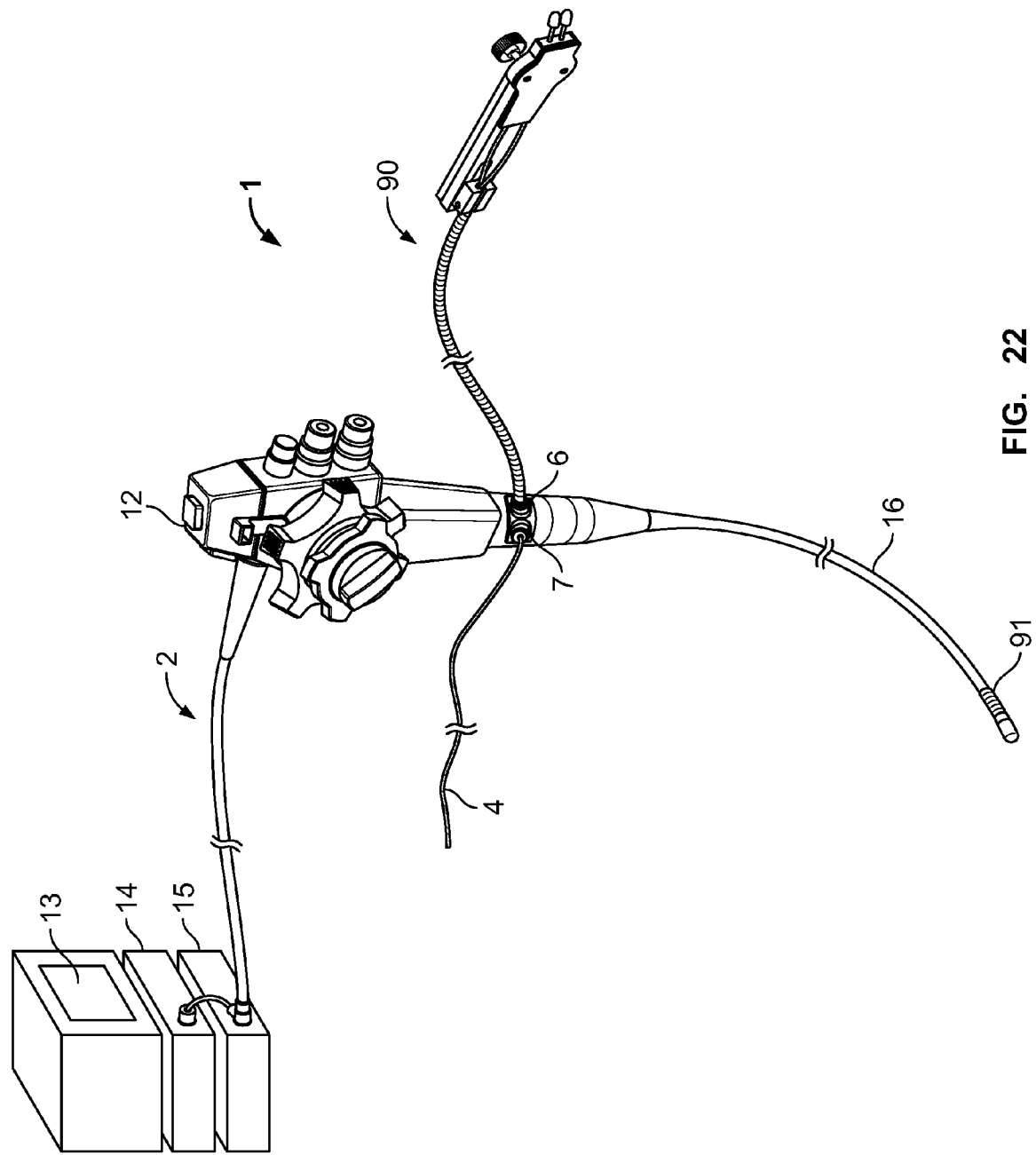
FIG. 22 shows an endoscopic suturing instrument according to a second embodiment.
Figure 23:
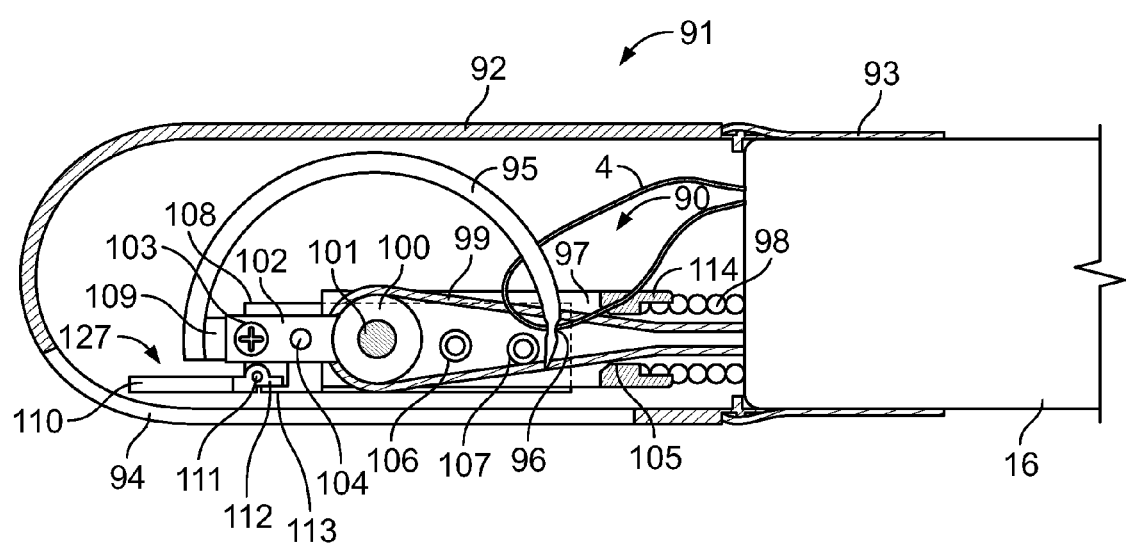
FIG. 23 is an enlarged sectional view of the distal end of the endoscope 12 with the suturing instrument according to the second embodiment.

FIG. 22 shows the entire makeup of the endoscopic suturing instrument system 1. FIG. 23 shows the distal end of the endoscope 12, enlarged for better understanding. As the makeup of the endoscope system 2 is the same as in example 1, an explanation is not given.

Figure 45:
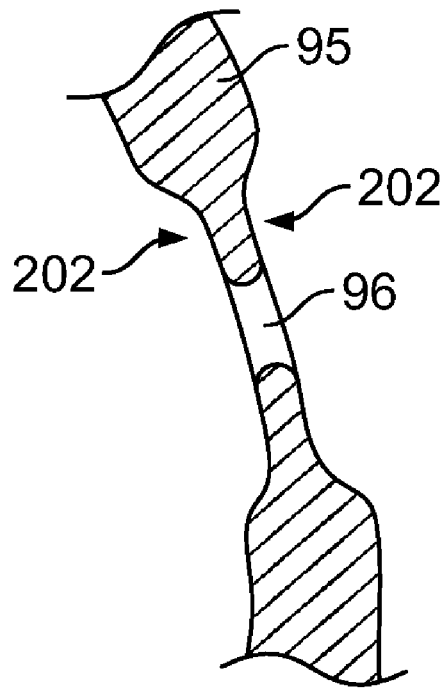
FIG. 45 shows a depression around the eye of the needle in the suturing instrument according to the second embodiment.

As shown in FIG. 22 and FIG. 23, the suturing instrument 90 is inserted in the instrument channel port 6. The thread 4, inserted through the needle eye 96 provided in the curved needle 95 of the suturing instrument 90, extends through the instrument channel port 7 to its proximal end. In this example, the suturing instrument 90 is provided in the instrument channel 6 of the video scope 12. However, it may also be built in the endoscope 12. Around the needle eye 96, a depressed portion 202 is formed, as shown in FIG. 45, in order to reduce puncture resistance.

As shown in FIG. 23, the tissue-protection member 91 consists of the protection portion 92, at least part of which is transparent, and the fixing portion 93 made of an elastomer resin such as silicon rubber, which is the same as explained in Example 1. The protection portion 92 is joined with the fixing portion 93 by injection or adhesion. The tissue protection member 91 thus constructed is detachably fixed to the flexible portion 16. This is implemented by pressing the fixing portion 93 into the distal end of the flexible portion 16. The protection portion 92 is provided with a slit 94 so that the curved needle 95, the needle puncture support means 127, and the thread 4 may pass through.

Figure 24:
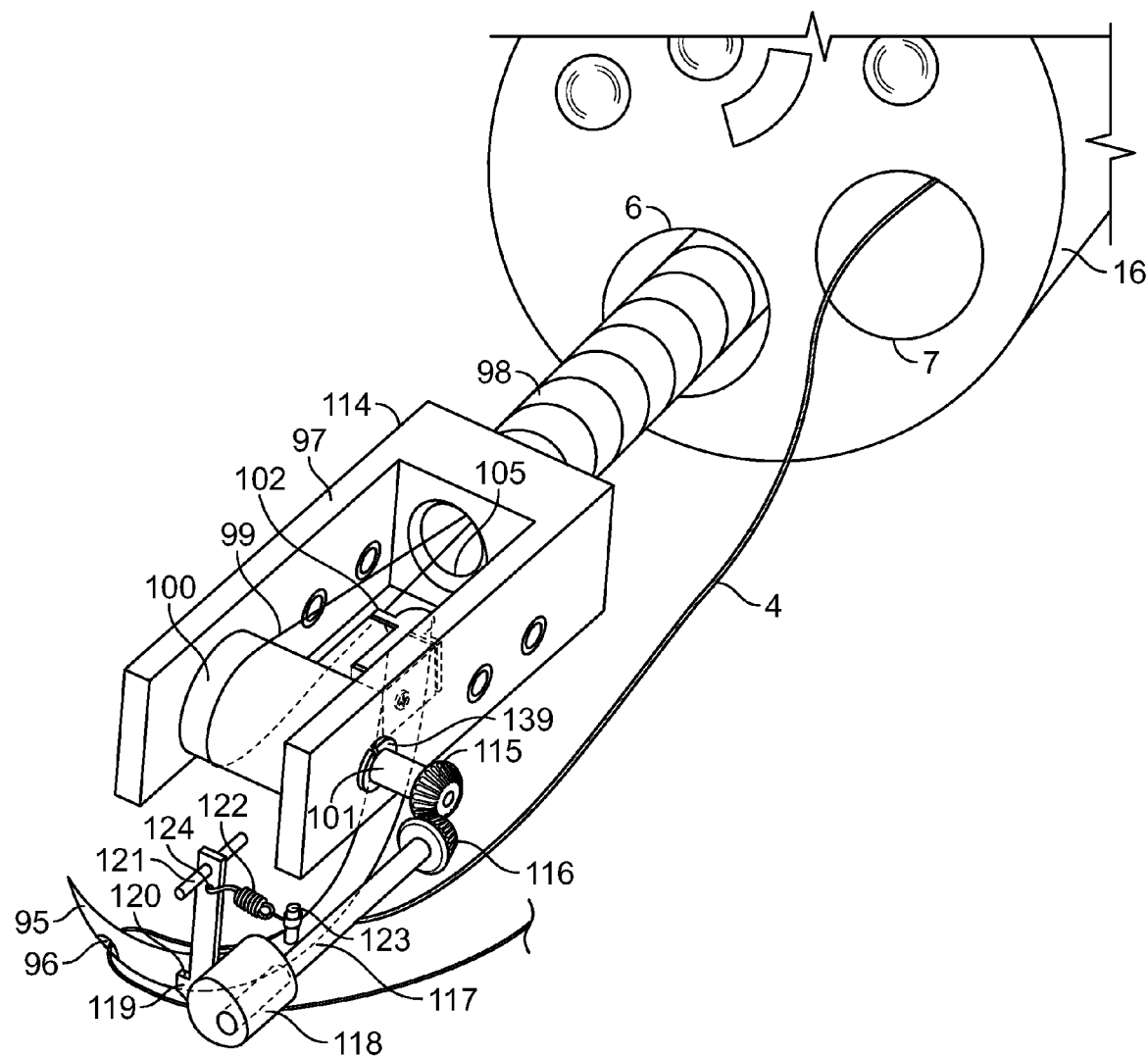
FIG. 24 shows a distal end of a suturing instrument according to the second embodiment.
Figure 30:
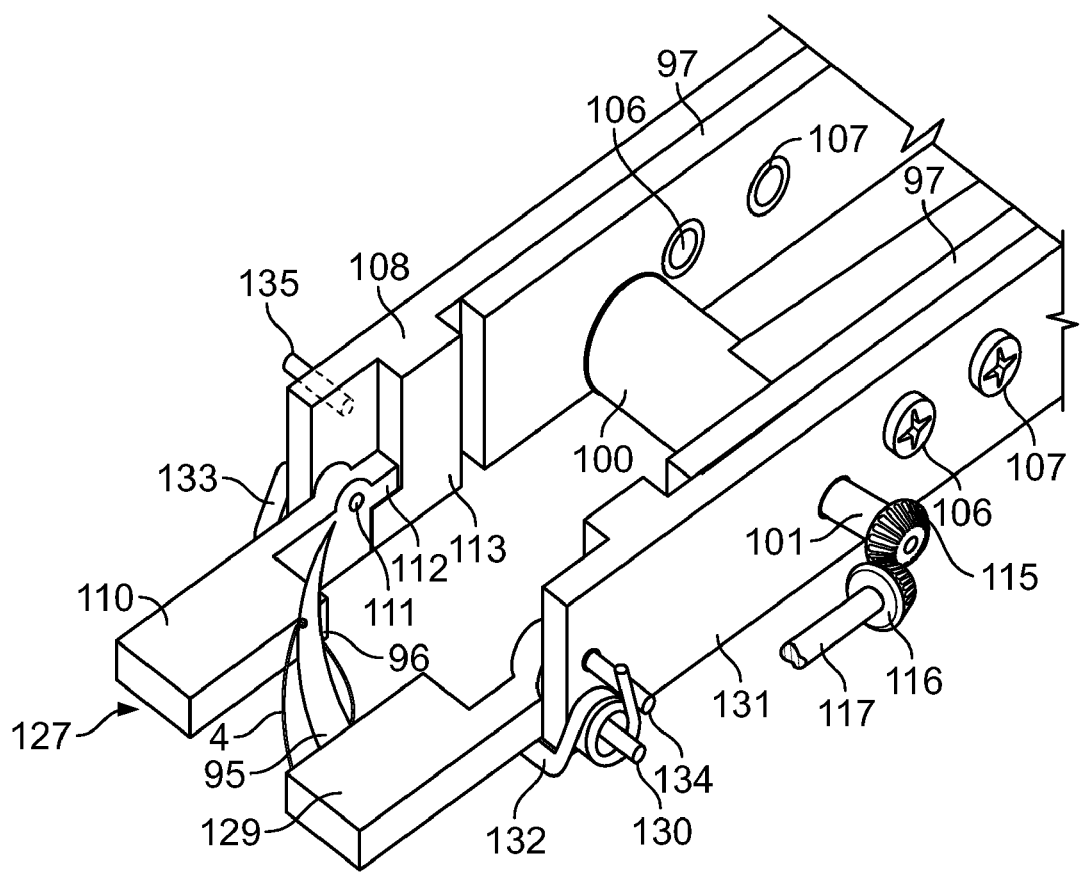
FIG. 30 shows a needle puncture support mechanism of the suturing instrument according to the second embodiment.
Figure 32:
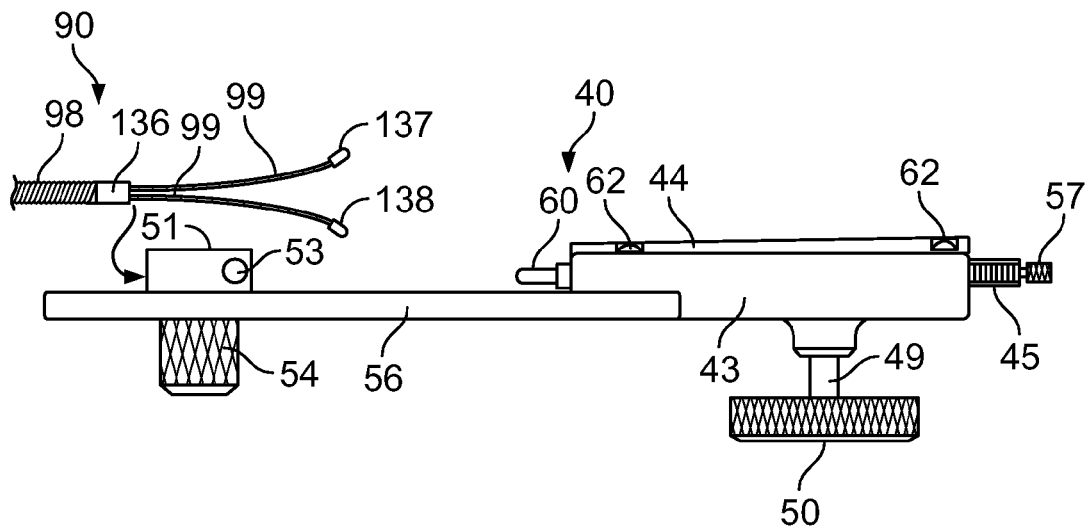
Figure 33:
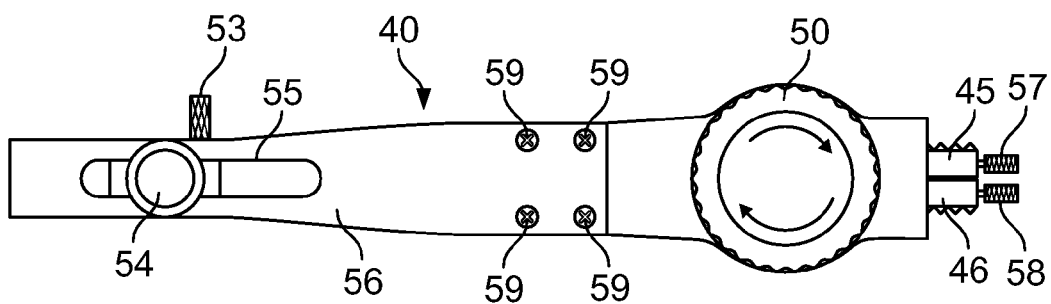
Figure 34:
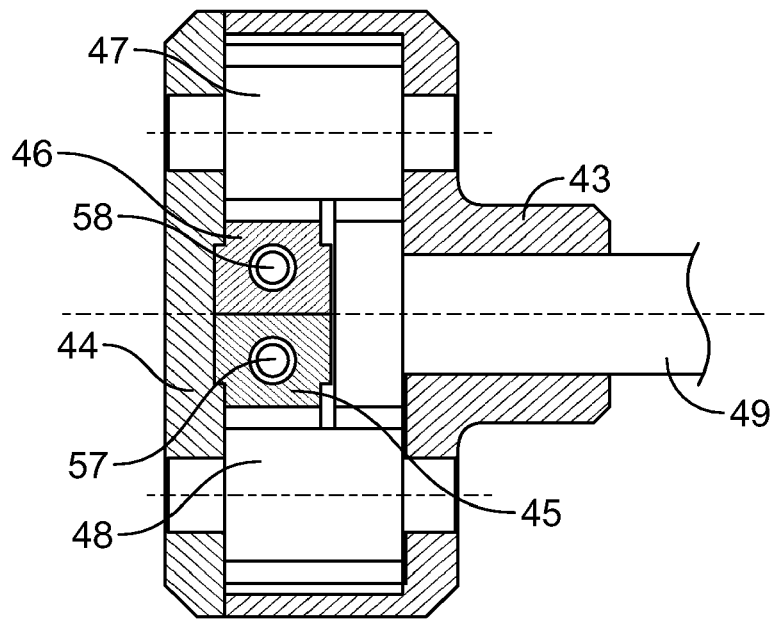
FIG. 34 is a sectional view of the operating portion of the suturing instrument of the second embodiment.
Figure 41:
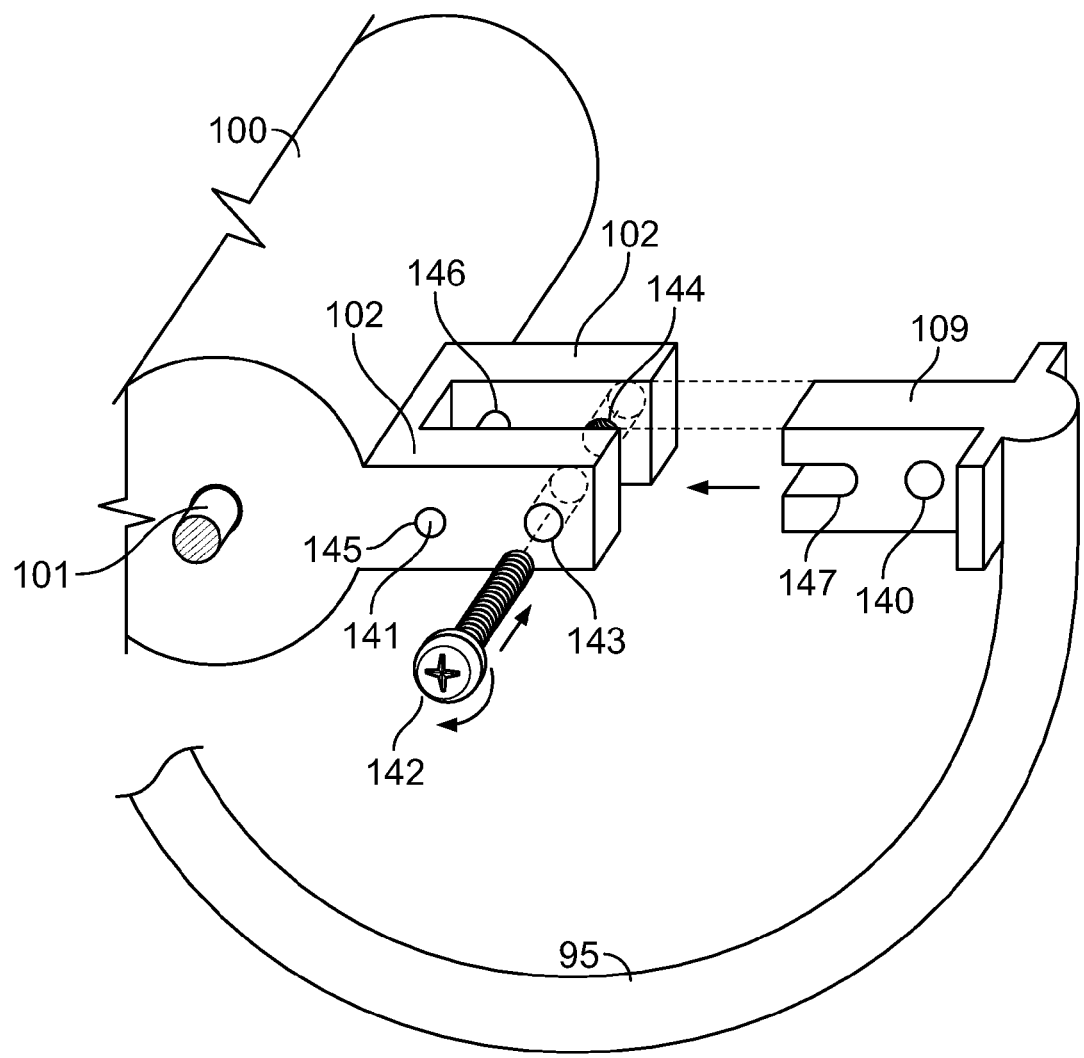
FIG. 41 shows the attachment of the needle in the suturing instrument according to the second embodiment.
Figure 42:
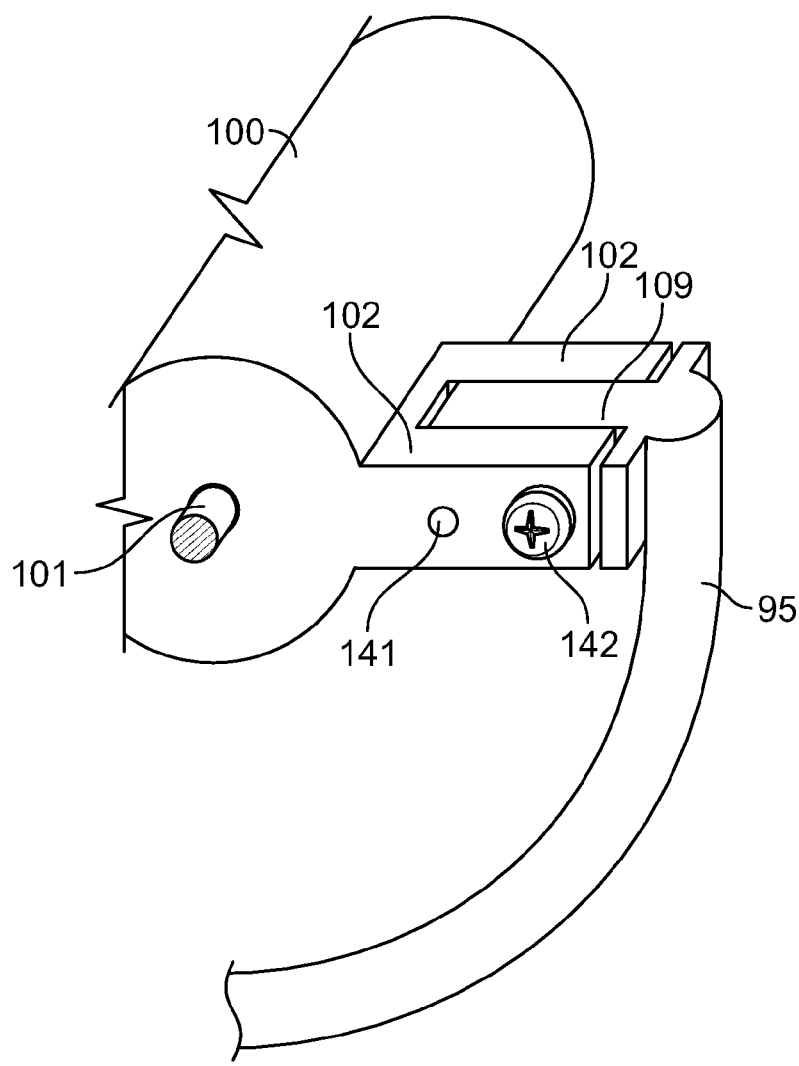
FIG. 42 shows the needle in place in the suturing instrument according to the second embodiment.
Figure 43:
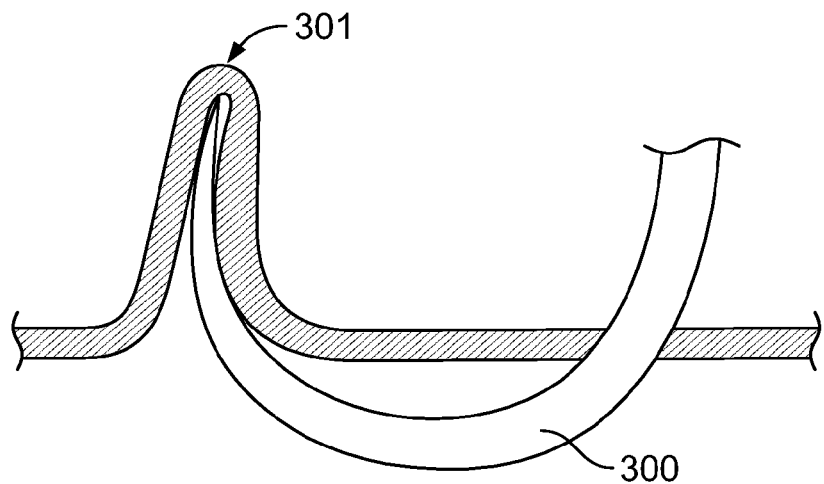
FIG. 43 shows a curved needle attempting to pierce tissue.

As shown in FIG. 22 through FIG. 24 and in FIG. 32, the suturing instrument 90 is equipped with a flexible coil 98 having a cavity inside, on the distal end of which a supporting member 114 is fixed. A sleeve member 136 having a cavity inside is provided at the proximal end of the flexible coil 98. The operating wire 99 is inserted through the flexible coil 98 and the sleeve member 136 and extends out through a hole 105 in the supporting member 114. As shown in FIG. 24, a clevis 97 is provided at the distal end of the supporting member 114. A disc 100, with which to rotate the curved needle 95, is equipped with an axis 101 integrated into it, both ends of which are supported by the clevis 97 of the supporting member 114. In addition, the stop member 139 is provided to prevent the clevis 97 from being expanded. As shown in FIG. 41 and FIG. 42, the disc 100 is equipped with a pair of arms 102, which are spanned by a pin 141. The pin 141 is inserted through the two holes 145 and 146 punched in the arms 102 and fixed to them. Furthermore, the hole 143 and female screw 144 are drilled at the distal end of the arms 102. The needle-holding member 109 is fixed to the proximal end of the curved needle 95, where a slit 147 that fits the pin 141 and a hole 140 through which a screw 142 is inserted are provided. Thus, the curved needle is detachably fixed by the pin 141 and the screw 142. As shown in FIG. 30, the needle puncture support means 127 consists of:

a pair of tissue-holding portions 110 and 129, holding members 108 and 131, where each of the tissue-holding portions 110 and 129 is held by a pin 111 and a pin 130, respectively, while being allowed to rotate freely, and springs 132 and 133, contact the tissue-holding portions 110 and 129 at one end thereof and abut against projections 135 and 134 at the other end thereof, which apply a force to keep the tissue-holding portions 110 and 129 constantly rotating in the same direction. Over-rotation of each of the tissue-holding portions 110 and 129 is stopped by a support 113 (shown with respect to tissue-holding portion 110) against which the end 112 of the tissue-holding portion 110 is made to abut.

In addition, the holding members 108 and 131 are fixed to the clevis 97 by screws 106 and 107.

The operating wire 99 is wound on the surface of the disc 100 at least once, and the wound part of the operating wire 99 is fixed to the edge of the disc 100 by brazing, soldering, or frictional resistance so that the force of the operating wire may be securely transmitted to the disc 100. The curved needle 95 is curved so that the center of the rotation of the curved needle 95 will almost agree with its center of curvature As shown in FIG. 24, a bevel gear 115 is fixed to one end of the axis 101 of the disc 100. The bevel gear 115 comes in contact with the bevel gear 116 fixed to the proximal end of the axis 117, which is placed at right angles to the axis 101 so as to transmit the driving force of the operating wire 99 to the axis 117. An eccentric cam 118 is fixed to the distal end of the axis 117. The thread catch member 119 having a hook 120 comes in contact with an axis 121 fixed to the protection portion 92 (not shown in FIG. 24) while being allowed to rotate freely and is pushed against the eccentric cam 118 by the spring 122, which is coupled to the thread catch member at hole 124 and is supported at support 123. The thread catch member 119 can catch the thread 4 when the eccentric cam 118 is rotated until it comes to the position shown in FIG. 25 and can release the thread 4 when the eccentric cam rotates to the position shown in FIG. 26.

Figure 31:
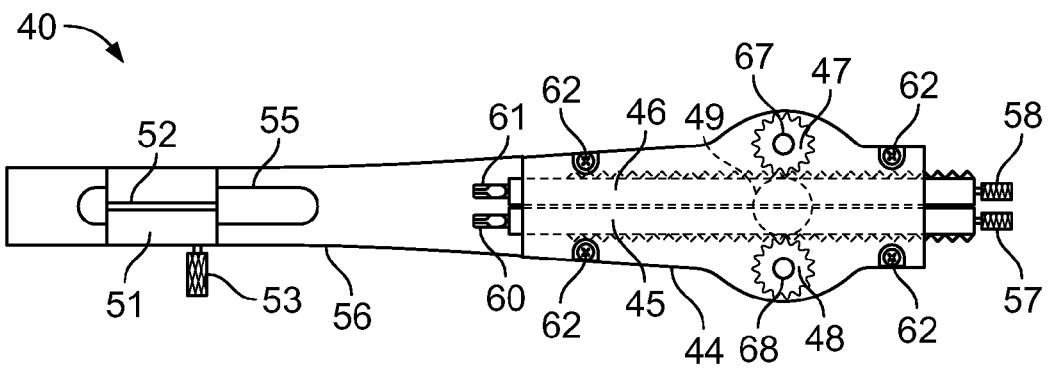
FIGS. 31, 32 and 33 show an operating portion of the suturing instrument of the second embodiment from three directions.
Figure 37:
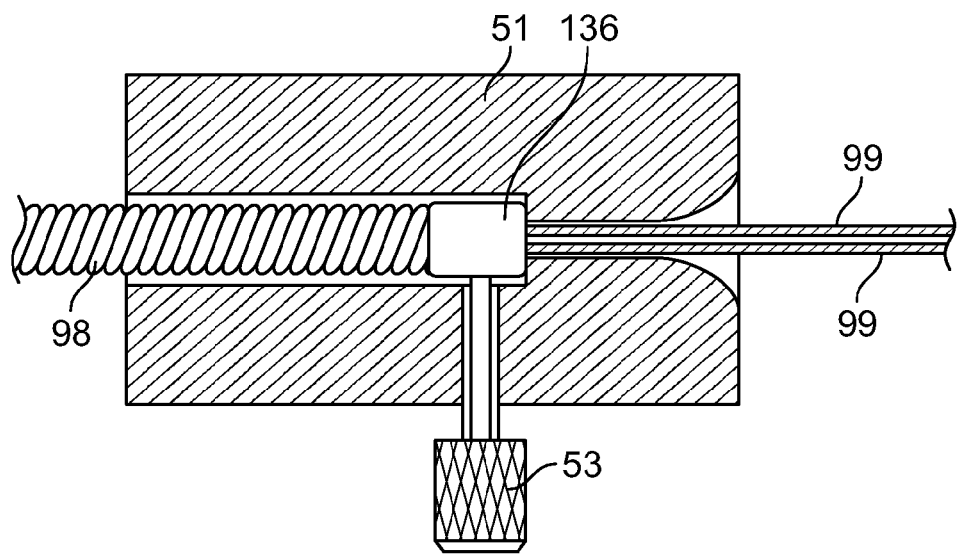
FIG. 37 shows the flexible coil 98 being fixed in place in the operating portion of the suturing instrument of the second embodiment.
Figure 38:
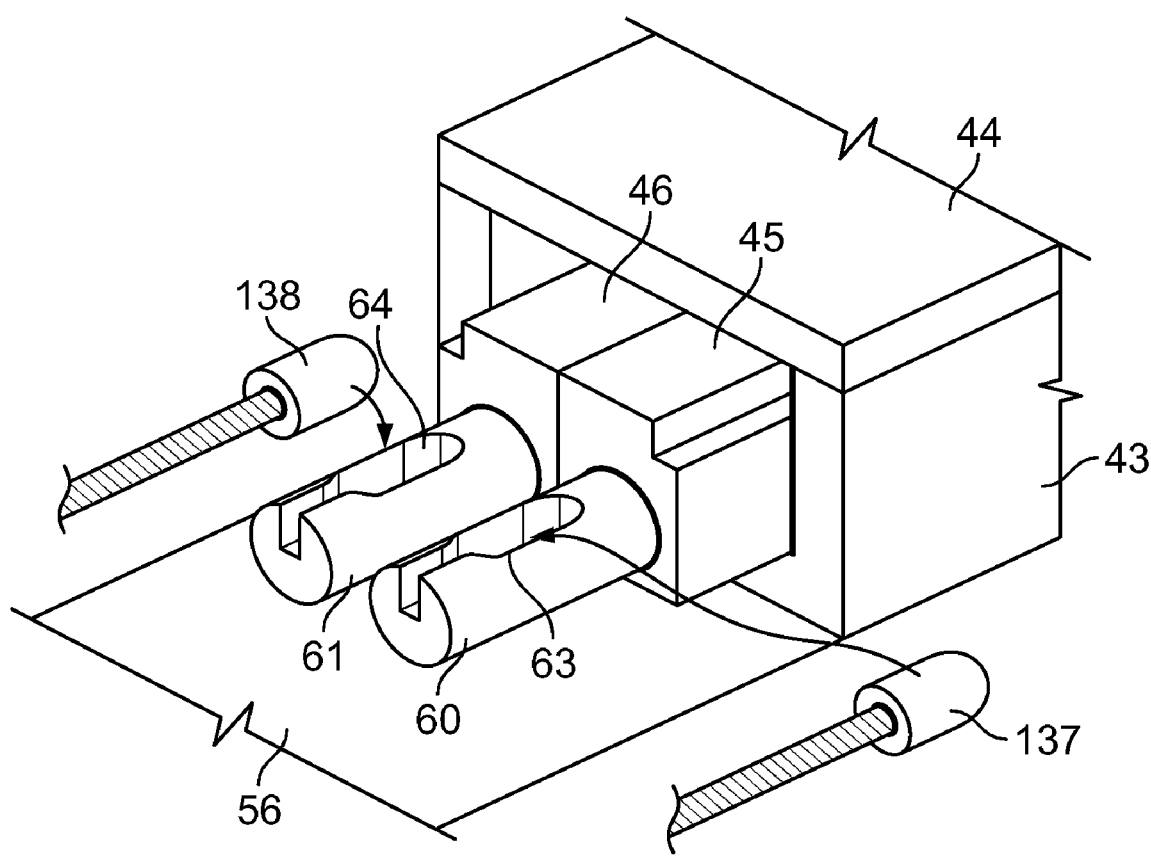
FIG. 38 shows the stoppers 137 and 138 being inserted into position in the operating portion of the suturing instrument of the second embodiment.
Figure 39A:
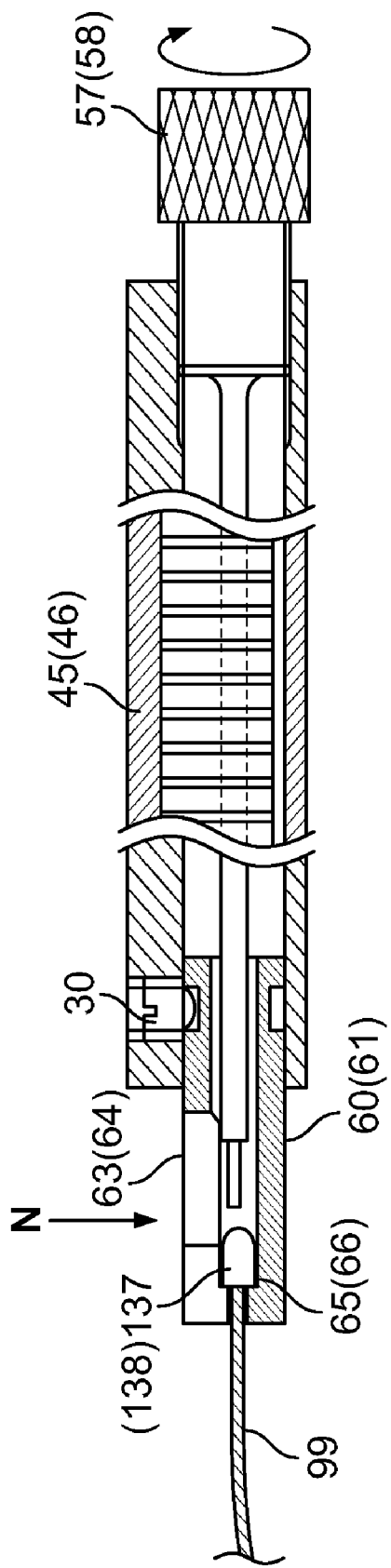
FIG. 39A is a side view showing the fixing in place of the stoppers 137 and 138 into the operating portion of the suturing instrument of the second embodiment.
Figure 39B:
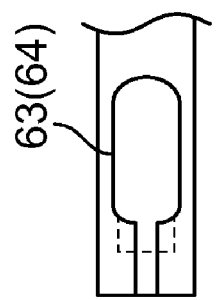
FIG. 39B is a view along direction N in FIG. 39A.

The operating portion 40 includes:

a housing 43 a plate 56 fixed to the housing 43 with four screws 59, a slider 51 that can freely slide or be fixed at any desired position by a combination of the oblong hole 55 punched in the plate 56 and the screw 54, two racks 45 and 46 placed in the housing 43 so as to be able to slide freely, two pinion gears 48 and 47 that come in contact with the racks 45 and 46, respectively, an axis 49 having a gear that meshes both gears 47 and 48 at the same time, a cover 44, which has holes 67 and 68 that fit the axes of pinion gears 47 and 48, respectively, and which is fixed to the housing 43 with screws 62, a handle 50 fixed to the end of the axis 49, as shown in FIG. 22 and FIG. 31 through FIG. 40, and stopper-fixing members 60 and 61 fixed to the racks 45 and 46, respectively, with screws 30, as shown in FIG. 31 and FIG. 39A.

Figure 35:
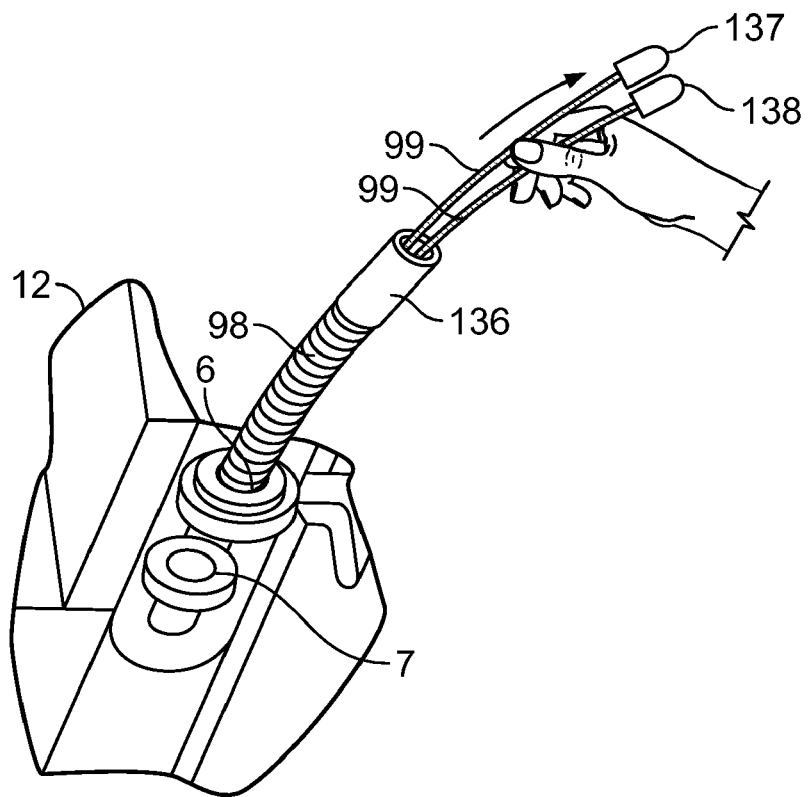
FIG. 35 shows stoppers 137 and 138 being pulled out of the instrument channel port 6.
Figure 36:
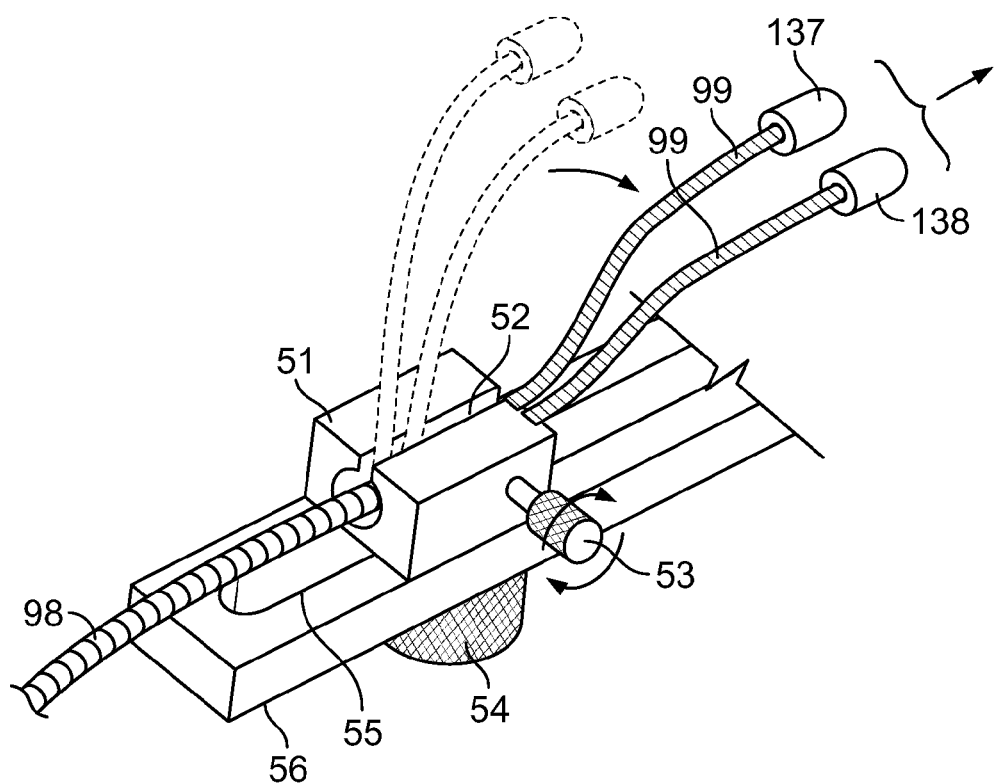
FIG. 36 shows stoppers 137 and 138 being introduced into the operating portion of the suturing instrument of the second embodiment.
Figure 40:
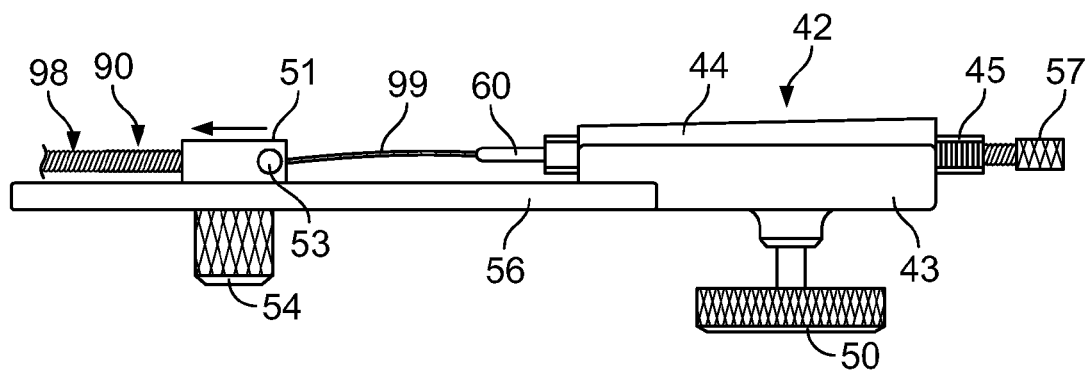
FIG. 40 shows applying tension to operating wires 99 in the operating portion of the suturing instrument of the second embodiment.

After the stoppers 137 and 138 are pulled out of the instrument channel port 6, as shown in FIG. 35, the operating wires 99 are inserted through the slit 52, as shown in FIG. 36, and then the sleeve member 136 is detachably fixed with a screw 53, as shown in FIG. 37. Then, the stoppers 137 and 138 are inserted in the ports 63 and 64 provided for the stopper-fixing members 60 and 61, as shown in FIG. 38. The stoppers 137 and 138 are then withdrawn to hit the mounts 65 and 66 provided for the stopper-fixing members 60 and 61, respectively, and are held with the screws 57 and 58 to prevent the stoppers 137 and 138 from escaping from the ports 63 and 64, as shown in FIG. 39A. Then, as shown in FIG. 40, the suturing instrument 3 fixed to the slider 51 by the screw 53 is slid in the direction of the arrow as shown in the diagram. With tension applied to the operating wires 99, the slider is fixed on the plate by the screw 54. The operating portion 40 with this structure changes the rotational movement of the handle 50 to a linear movement of the racks 45 and 46 through the axis 49 and the pinion gears 47 and 48, allowing the operating wires 99 to be pushed backward and forward, the curved needle to rotate, and the thread catch member 119 to move.

As shown in FIG. 24, with the thread 4 inserted through the needle eye 96 of the curved needle 95, the handle 50, as shown in FIG. 40, is rotated clockwise to puncture the tissue with the curved needle 95. The handle 50 is further rotated clockwise until the curved needle 95 is rotated to reach the position shown in FIG. 27. Then, the handle 50 is rotated counterclockwise to restore the curved needle to the position shown in FIG. 28, where a loop 126 is formed in the thread 4 at the distal end of the curved needle 95. Immediately after the loop 126 is formed, the eccentric cam 118 moves the thread catch member 119 to the position where the hook 120 will go into the loop 126.

Figure 25:
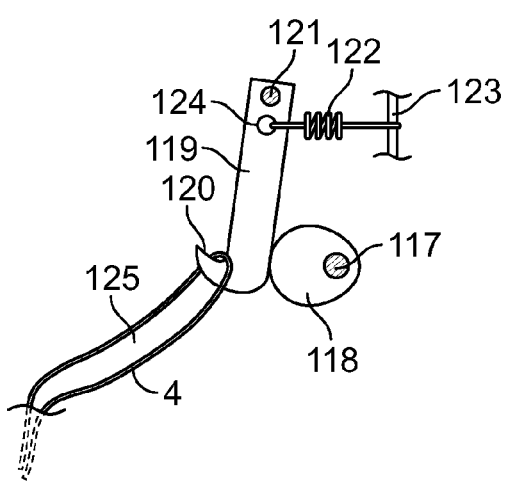
FIGS. 25–29 show a suturing procedure with the suturing instrument according to the second embodiment.

Then, the handle 50 is further rotated counterclockwise until the curved needle reaches the position shown in FIG. 23, when the thread catch member 119 has been set by the eccentric cam 118 to the position where it can keep holding the thread 4, as shown in the FIG. 25. When the suturing instrument 90 is moved to the next suture site with the thread caught by the hook 120, a loop 125 is formed, as shown in FIG. 25.

Figure 26:
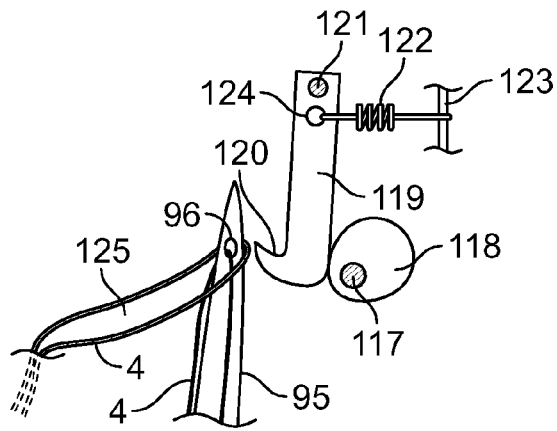

Then, the handle 50 is rotated clockwise again to puncture the tissue with the curved needle 95, and the curved needle 95 will pass through inside of the loop 125 as shown in FIG. 26. After this, the thread catch member 119 is moved by 118 counterclockwise to release the thread 4 from the hook 120.

Figure 27:
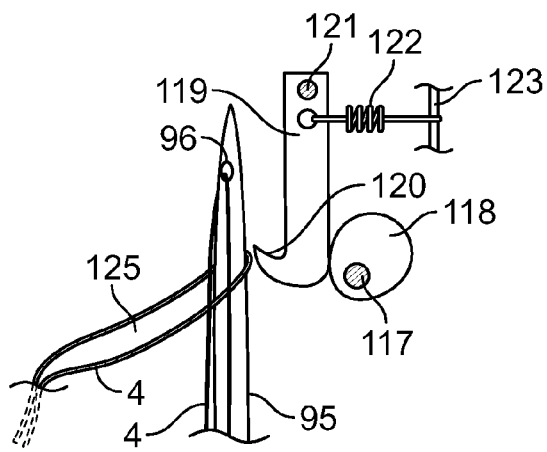
Figure 28:
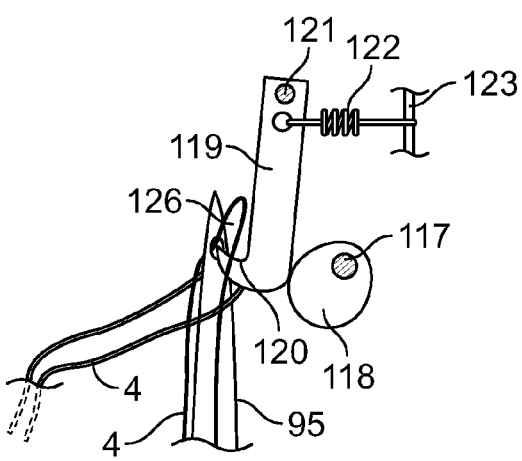

The handle 50 is further rotated clockwise to rotate the curved needle until it comes to the position shown in FIG. 27. Then, the handle 50 is rotated counterclockwise to restore the curved needle to the position shown in FIG. 28, when a loop 126 is formed in the thread 4 at the distal end of the curved needle, as explained above. Immediately after the loop 126 is formed, the thread catch member 119 is moved by the eccentric cam 118 to the position where the hook 120 will go into the loop 126.

After this, the operation, as shown in FIG. 25 through FIG. 28, is repeated to implement continuous stitches similar to those shown in FIG. 19 in Example 1.

Figure 29:
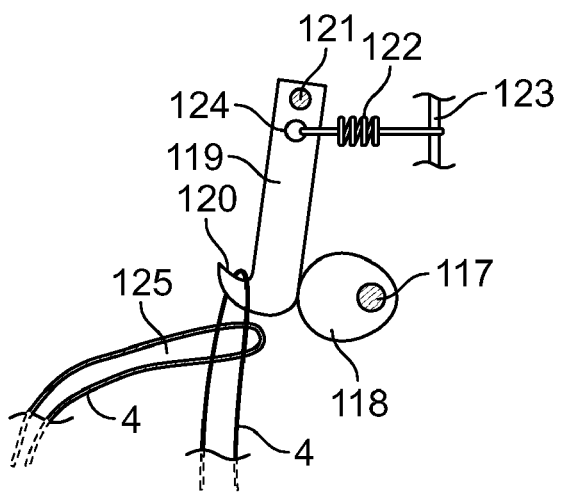

In the last stitch, as shown in FIG. 29, the flexible portion 16 is removed from the living body with the curved needle 95 withdrawn from the tissue, and the thread pulled out from the lumen is ligated with the ligating members 80 and 83, as shown in FIG. 20 and FIG. 21, in the same way as explained in Example 1.

This embodiment of Example 2 also has a number of advantages as follows:

The tissue is sequentially stitched through a flexible endoscope.

Held securely in the needle-fixing portion, the needle will not come off as it often does from the needle holder. Thus, the needle accurately punctures the tissue without fail.

Since the need for alternately re-holding the needle is eliminated, operation is simpler.

The needle puncture support means is provided to hold the tissue tightly when the curved needle punctures the tissue so that the curved needle will accurately puncture the tissue.

There is no limitation to the length of thread to be loaded, so long wounds may be sutured in continuous stitches while the endoscopic view is seldom disturbed.

The needle is detachable from the needle-fixing portion so that disposable needles may be used.

The depth of the puncture can be controlled by adjusting the radius of the curvature of the needle.

The position where the needle punctures the tissue and the position where the needle comes out from the tissue can be confirmed under endoscopic view.

The suture is performed both in the forward direction and along a tangent to the endoscopic view.

Thus, overall, embodiments of the present invention provide improvements which include the following:

The tissue is sequentially stitched through a flexible endoscope.

Held securely in the needle-fixing portion, the needle will not come off as it often does from the needle holder. Thus, the needle accurately punctures the tissue without fail.

Since the need for alternately re-holding the needle is eliminated, operation is simpler.

There is no limitation to the length of thread to be loaded, so long wounds may be sutured in continuous stitches while the endoscopic view is seldom disturbed during suturing procedures.

The needle is detachable from the needle-fixing portion so that disposable needles may be used.

The tissue-protection member mounted on the distal end of the insertion portion allows the suturing instrument to be inserted in the target site without any danger of the lumen surface being damaged by the needle.

The makeup of the suturing instrument reduces puncture resistance, allowing punctures deep into the tissue.

The suturing instrument can be used through the instrument channel port of an endoscope, providing easy suture operation in a small lumen.

A general-purpose endoscope may be used in the operation of the suturing instrument, which contributes to cost reduction.

As it is an independent instrument, it may be cleaned, disinfected, and sterilized in the same way as existing ET products.

The operating portion is detachable so that the suturing instrument, having an external diameter larger than the instrument channel port, may be mounted on the endoscope. Furthermore, the operating portion may be shared, or any portion other than the operating portion may be made disposable.

The tissue is held tight during the suturing procedure when the suction function of the endoscope is used so that the suturing procedure is easier.

When a curved needle is used, the depth of the puncture can be controlled by adjusting the radius of the curvature of the needle.

When a curved needle is used, the position where the needle punctures the tissue and the position where the needle comes out from the tissue can be confirmed under endoscopic view.

When a curved needle is used, the suture is performed both in the forward direction and along a tangent to the endoscopic view.

What is claimed is:

1. An endoscopic suturing instrument comprising:
   a needle provided at a distal end of the suturing instrument for puncturing living tissue;
   an engaging section provided at least at a distal end of the needle for engaging thread while allowing the thread to move freely;
   a needle-driving mechanism to drive the needle;
   a loop-creating mechanism which creates a first loop in the thread by loosening the thread connected to the engaging section;

a catching member to be inserted through said first loop to catch said thread disposed at the distal end of said suturing instrument body;

wherein the thread caught by said catching member is freely movable, and the needle-driving mechanism and the catching member are mechanically coupled;

wherein the loop-creating mechanism is also used to create a second loop with the thread by loosening the thread between the living tissue and the catching member, and a locus of movement of the needle passes through the second loop;

wherein the loop-creating mechanism comprises a cam mechanism which is operable such that the thread is released from the catching member when at least a part of the needle passes through the second loop, after which the catching member is inserted through the first loop created by the loop-creating mechanism so as to catch the thread; and wherein the cam mechanism includes a cam and at least one spring member to direct the cam in a single direction.

2. An endoscopic suturing instrument according to claim 1 wherein the spring member is a made of an elastic material.

3. An endoscopic suturing instrument comprising:
a needle provided at a distal end of the suturing instrument for puncturing living tissue;
an engaging section provided at least at a distal end of the needle for engaging thread while allowing the thread to move freely;
a needle-driving mechanism to drive the needle;
a loop-creating mechanism which creates a first loop in the thread by loosening the thread connected to the engaging section;
a catching member to be inserted through said first loop to catch said thread disposed at the distal end of said suturing instrument body;
wherein the thread caught by said catching member is freely movable, and the needle-driving mechanism and the catching member are mechanically coupled; and
wherein the needle comprises a curved needle.

4. An endoscopic suturing instrument according to claim 3, further comprising a protecting member at a distal end of one of the suturing instrument and an endoscope used with the suturing instrument, wherein the protect member protects the living tissue from the curved needle when the suturing instrument is inserted into a living body.

5. An endoscopic suturing instrument comprising:
a needle movably provided at a distal end of the suturing instrument for puncturing living tissue;
an engaging section provided at least at an end of the needle for movably engaging thread;
an elongated needle driving member which extends to a proximal end of the suturing instrument, and which is operable to move the needle to puncture tissue to be sutured;
a thread catcher which is provided at the distal end of the suturing instrument, and which catches the thread to form a loop of the thread at a position where the thread is passed through the tissue with the needle; and
a thread catcher driver which is mechanically interlocked with the elongated needle driving member, and which is adapted to move the thread catcher to catch the thread;
wherein both the needle and the thread catcher driver are driven by movement of the elongated needle driving member.

6. The endoscopic suturing instrument according to claim 5, wherein the thread catcher driver comprises a cam mechanism that moves the thread catcher between a first position where the thread catcher catches the thread and a second position where the thread catcher releases the thread.

7. The endoscopic suturing instrument according to claim 6, wherein the cam mechanism includes a cam and at least one spring member adapted to direct the cam in a single direction.

8. The endoscopic suturing instrument according to claim 7, wherein the spring member is made of an elastic material.

9. The endoscopic suturing instrument according to claim 5, wherein the suturing instrument is adapted to be pulled out of a living body with the thread catcher holding the thread.

10. The endoscopic suturing instrument according to claim 5, wherein the thread catcher is shaped as a hook.

11. The endoscopic suturing instrument according to claim 5, further comprising means for preventing the thread from loosening so as not to allow the thread to become loose after suturing.

12. The endoscopic suturing instrument according to claim 11, wherein the preventing means is adapted to tie up both ends of the thread at least once.

13. The endoscopic suturing instrument according to claim 11, wherein the preventing means comprises a thread-holding member on each end of the thread.

14. The endoscopic suturing instrument according to claim 13, wherein the thread-holding member includes a pair of arms to grasp thread.

15. the endoscopic suturing instrument according to claim 5, further comprising a flexible endoscope for use with the suturing instrument.

16. The endoscopic suturing instrument according to claim 5, wherein the needle comprises a straight needle.

17. The endoscopic suturing instrument according to claim 5, wherein the needle comprises a curved needle.

18. The endoscopic suturing instrument according to claim 17, further comprising a protecting member that covers at least a part of the curved needle to protect the living tissue when the suturing instrument is inserted into a living body.

19. The endoscopic suturing instrument according to claim 5, further comprising a needle-thrust-out supporting mechanism on a side where the needle will thrust out from the tissue so that the needle may thrust through the tissue when the needle punctures a suture site.

20. The endoscopic suturing instrument according to claim 19, wherein the needle-thrust-out supporting mechanism is allowed to move toward the side where the needle will thrust out from the tissue and is not allowed to move toward an opposite side.

21. The endoscopic suturing instrument according to claim 5, further comprising a fixing mechanism to fix the living tissue and the suturing instrument temporarily.

22. A suturing method allowing continuous stitches in a body cavity using an endoscopic suturing instrument, wherein the endoscopic suturing instrument comprises: a needle movably provided at a distal end of the suturing instrument for puncturing living tissue, an engaging section provided at least at a sharp end of the needle for movably engaging thread, an elongated needle driving member which extends to a proximal end of the suturing instrument and which is operable to move the needle to puncture tissue to be sutured, a thread catcher which is provided at the distal end of the suturing instrument and which catches the thread to form a loop of the thread at a position where the thread is passed through the tissue with the needle, and a thread catcher driver which is mechanically interlocked with the elongated needle driving member and which is adapted to move the thread catcher to catch the thread, wherein both the needle and the thread catcher driver are driven by movement of the elongated needle driving member, said method comprising:

a. connecting the thread to the engaging section;
b. moving the suturing instrument to a first suture site of the living tissue;
c. moving the needle to a first position at which puncturing is not performed on the living tissue;
d. moving the needle with the thread to a second position at which the needle thrusts out through the living tissue so that the thread comes out from the living tissue;
e. moving the needle further along a direction of puncturing to a third position;
f. returning the needle to the second position to create a first loop in the thread;
g. catching the first loop with the thread catcher;
h. moving the needle to the first position with the first loop caught by the thread catcher;
i. moving the suturing instrument to a second suture site of the living tissue;
j. creating a second loop between the living tissue and the thread catcher;
k. moving the needle to the second position again;
l. passing the needle through the second loop;
m. removing the thread catcher from the thread forming the second loop when a part of the needle passes through the second loop;
n. moving the needle further along the direction of puncturing to the third position;
o. returning the needle to the second position to create the first loop in the thread;
p. catching the first loop with the thread catcher again;
q. repeating steps h through p at least once;
r. removing the suturing instrument from the body cavity with the thread caught by the thread catcher; and
s. stopping both ends of the thread that extend from the living tissue to prevent the thread from loosening.

* * * * *